US012661182B2

(12) United States Patent
Morvan et al.

(10) Patent No.: US 12,661,182 B2
(45) Date of Patent: Jun. 23, 2026

(54) POSITIONING A CAMERA FOR PERSPECTIVE SHARING OF A SURGICAL SITE

(71) Applicant: HOWMEDICA OSTEONICS CORP., Mahwah, NJ (US)

(72) Inventors: Yannick Morvan, Saint Renan (FR); Damien Cariou, Loperhet (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 720 days.

(21) Appl. No.: 17/629,013

(22) PCT Filed: Jul. 23, 2020

(86) PCT No.: PCT/US2020/043218
§ 371 (c)(1),
(2) Date: Jan. 21, 2022

(87) PCT Pub. No.: WO2021/016429
PCT Pub. Date: Jan. 28, 2021

(65) Prior Publication Data
US 2022/0265357 A1 Aug. 25, 2022

Related U.S. Application Data

(60) Provisional application No. 62/878,573, filed on Jul. 25, 2019.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 90/36* (2016.02);
(Continued)

(58) Field of Classification Search
CPC ......... A61B 34/10; A61B 34/20; A61B 34/25; A61B 90/36; A61B 90/361;
(Continued)

(56) References Cited

U.S. PATENT DOCUMENTS 7,471,821 B2 * 12/2008 Rubbert ................. B33Y 80/00
382/128
2012/0122062 A1 * 5/2012 Yang ......................... G09B 9/00
434/219
(Continued)

OTHER PUBLICATIONS

"Blueprint 3d Planning Software + PSI," Wright Medical Group, retrieved from https://www.wright.com/blueprint-3d-planning-psi-system on Oct. 15, 2020, 9 pp.
(Continued)

*Primary Examiner* — Michael Le
(74) *Attorney, Agent, or Firm* — Shumaker & Sieffert, P.A.

(57) ABSTRACT

Techniques for augmenting a view of a first user of a first mixed reality (MR) visualization device in an operating room are described. For example, an intraoperative guidance system is configured to determine a location for a second user to stand within the operating room. A second MR visualization device is configured to be worn by the second user. The second MR visualization device is further configured to present a MR visualization that indicates the location for the second user to stand within the operating room. The first MR visualization device is configured to present a MR visualization that contains a window that show images of a surgical site captured by a camera supported by the second user.

25 Claims, 19 Drawing Sheets

(51) Int. Cl.
    *A61B 34/20*       (2016.01)
    *A61B 90/00*       (2016.01)

(52) U.S. Cl.
    CPC ...... *A61B 90/361* (2016.02); *A61B 2034/252*
        (2016.02); *A61B 2090/364* (2016.02); *A61B*
              *2090/365* (2016.02)

(58) Field of Classification Search
    CPC ........ A61B 2034/252; A61B 2090/364; A61B
                         2090/365
    See application file for complete search history.

(56) References Cited

U.S. PATENT DOCUMENTS

| | | | |
|---|---|---|---|
| 2014/0276855 A1 | 9/2014 | de la Barrera et al. | |
| 2017/0143442 A1* | 5/2017 | Tesar | H04N 23/63 |
| 2017/0258526 A1* | 9/2017 | Lang | A61F 2/32 |
| 2018/0032130 A1 | 2/2018 | Meglan | |
| 2018/0078316 A1* | 3/2018 | Schaewe | A61B 34/20 |
| 2018/0197624 A1* | 7/2018 | Robaina | A61B 5/1171 |
| 2019/0011703 A1* | 1/2019 | Robaina | G02B 27/01 |
| 2019/0038362 A1* | 2/2019 | Nash | A61B 34/20 |
| 2019/0076198 A1* | 3/2019 | Berend | A61B 34/30 |
| 2020/0138518 A1* | 5/2020 | Lang | A61B 90/37 |
| 2020/0289217 A1* | 9/2020 | Denlinger | A61B 34/74 |
| 2021/0093385 A1* | 4/2021 | Morvan | A61B 90/90 |
| 2021/0093415 A1* | 4/2021 | Moore | A61B 17/142 |
| 2022/0211444 A1* | 7/2022 | Dassonville | A61B 34/20 |

OTHER PUBLICATIONS

"Hololens 2," Microsoft Hololens, retrieved from https://www.microsoft.com/en-us/hololens, on Oct. 15, 2020, 5 pp.
Adluru et al., "Merging maps of multiple robots," 2008 19th International Conference on Pattern Recognition, Dec. 2008, 4 pp.

Boissonnat, J.D., "Shape Reconstruction from Planar Cross Sections," Computer Vision, Graphics, and Image Processing, vol. 44, No. 1, Oct. 1988, 29 pp.
International Preliminary Report on Patentability from International Application No. PCT/US2020/043218, dated Feb. 3, 2022, 8 pp.
International Search Report and Written Opinion of International Application No. PCT/US2020/043218, dated Oct. 14, 2020, 13 pp.
Marker et al., "Contour-Based Surface Reconstruction using Implicit Curve Fitting, and Distance Field Filtering and Interpolation," vol. Graphics, Jan. 2006, 9 pp.
Nguyen et al., "A new segmentation method for MRI images of the shoulder joint," Fourth Canadian Conference on Computer and Robot Vision (CRV'07), May 2007, 8 pp.
Wright Medical, "BluePrint Video-Wright Medical Announces the Acquisition of IMASCAP SAS", accessed from www.mascap.com/wp-content/uploads/2017/12/blueprintvid.mp4, Dec. 14, 2017, 9 pp.
Wright, "BluePrint, 3d Planning + PSI," User Manual V2.1, Torier, CAW-8754, Nov. 2017, 18 pp.
Notice of Intent to Grant and Text Intended to Grant from counterpart European Application No. 20754490.9 dated Apr. 17, 2024, 162 pp.
Examination Report No. 1 from counterpart Australian Application No. 2020316076 dated Jan. 27, 2023, 3 pp.
Notice of Intent to Grant from counterpart Australian Application No. 2020316076 dated Sep. 5, 2023, 137 pp.
Response to Communication Pursuant to Rules 161(1) and 162 EPC dated Mar. 4, 2022, from counterpart European Application No. 20754490.9, filed Aug. 23, 2022, 22 pp.
Response to Office Action dated Jan. 27, 2023, from counterpart Australian Application No. 2020316076 filed Aug. 24, 2023, 137 pp.
Second Notice of Intent to Grant and Text Intended to Grant from counterpart European Application No. 20754490.9 dated Sep. 17, 2024, 85 pp.

\* cited by examiner

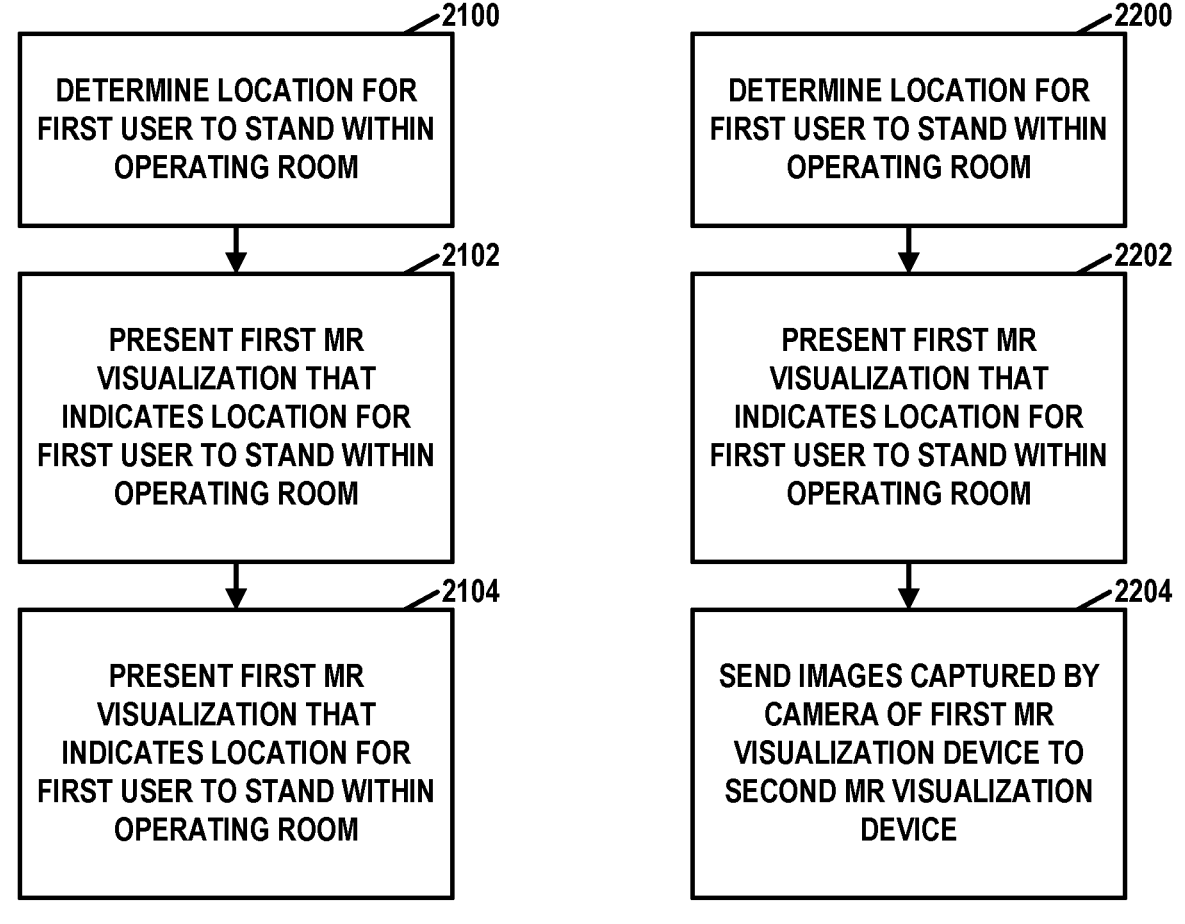
FIG. 21                    FIG. 22

POSITIONING A CAMERA FOR PERSPECTIVE SHARING OF A SURGICAL SITE

BACKGROUND

This application is a national stage application under 35 U.S.C. § 371 of PCT Application No. PCT/US2020/043218, filed Jul. 23, 2020, which claims the benefit of U.S. Provisional Application No. 62/878,573, filed Jul. 25, 2019.

Surgical joint repair procedures involve repair and/or replacement of a damaged or diseased joint. Many times, a surgical joint repair procedure, such as joint arthroplasty as an example, involves replacing the damaged joint with a prosthetic that is implanted into the patient's bone. Proper selection of a prosthetic that is appropriately sized and shaped and proper positioning of that prosthetic to ensure an optimal surgical outcome can be challenging. To assist with positioning, the surgical procedure often involves the use of surgical instruments to control the shaping of the surface of the damaged bone and cutting or drilling of bone to accept the prosthetic.

SUMMARY

This disclosure describes a variety of techniques for providing preoperative planning, medical implant design and manufacture, intraoperative guidance, postoperative analysis, and/or training and education for surgical joint repair procedures. The techniques may be used independently or in various combinations to support particular phases or settings for surgical joint repair procedures or provide a multi-faceted ecosystem to support surgical joint repair procedures. In various examples, the disclosure describes techniques for preoperative surgical planning, intra-operative surgical planning, intra-operative surgical guidance, intra-operative surgical tracking and post-operative analysis using mixed reality (MR)-based visualization. In some examples, the disclosure also describes surgical items and/or methods for performing surgical joint repair procedures.

In accordance with the techniques of this disclosure, an intraoperative guidance system is configured to determine a location for a first user to stand within an operating room. A first MR visualization device may be worn by the first user and may be configured to present a first MR visualization that indicates the location for the first user to stand within the operating room. A second MR visualization device may be worn by a second user and may be configured to present a second MR visualization that shows one or more images captured by a camera supported by the first user. This may help the second user obtain a different perspective on a surgical site.

In one example, this disclosure describes a MR surgical system, comprising: a first MR visualization device configured to be worn by the first user; a second MR visualization device configured to be worn by a second user; an intraoperative guidance system comprising one or more processing circuits configured to determine a location for the second user to stand within an operating room, wherein: the second MR visualization device is further configured to present a first MR visualization that indicates the location for the second user to stand within the operating room; and the first MR visualization device is further configured to present a second MR visualization that shows one or more images of a surgical site captured by a camera supported by the second user.

In another example, this disclosure describes a method for augmenting a view of a first user of a first mixed reality (MR) visualization device, the method comprising: determining a location for a second user to stand within an operating room; presenting, by a second MR visualization device configured to be worn by the second user, a MR visualization that indicates the location for the second user to stand within the operating room; and presenting, by the first MR visualization device, a MR visualization that contains a window that shows images of a surgical site captured by a camera supported by the second user while the second user is at the determined location.

In another example, this disclosure describes a method for augmenting a view of a first user of a first Mixed Reality (MR) visualization device, the method comprising: determining a location for a second user to stand within an operating room; presenting, by a second MR visualization device, a first MR visualization that indicates a location for a second user to stand within the operating room; and sending, by the second MR visualization device, image data representing images of a surgical site captured by a camera of the second MR visualization device to the first MR visualization device.

The details of various examples of the disclosure are set forth in the accompanying drawings and the description below. Various features, objects, and advantages will be apparent from the description, drawings, and claims.

BRIEF DESCRIPTION OF THE DRAWINGS

FIG. 21 is a flowchart illustrating an example operation for augmenting a view of a user of a MR visualization device, in accordance with one or more techniques of this disclosure.

FIG. 22 is a flowchart illustrating an example operation of an MR visualization device for augmenting a view of a user of another MR visualization device, in accordance with one or more techniques of this disclosure.

DETAILED DESCRIPTION

Figure 1:
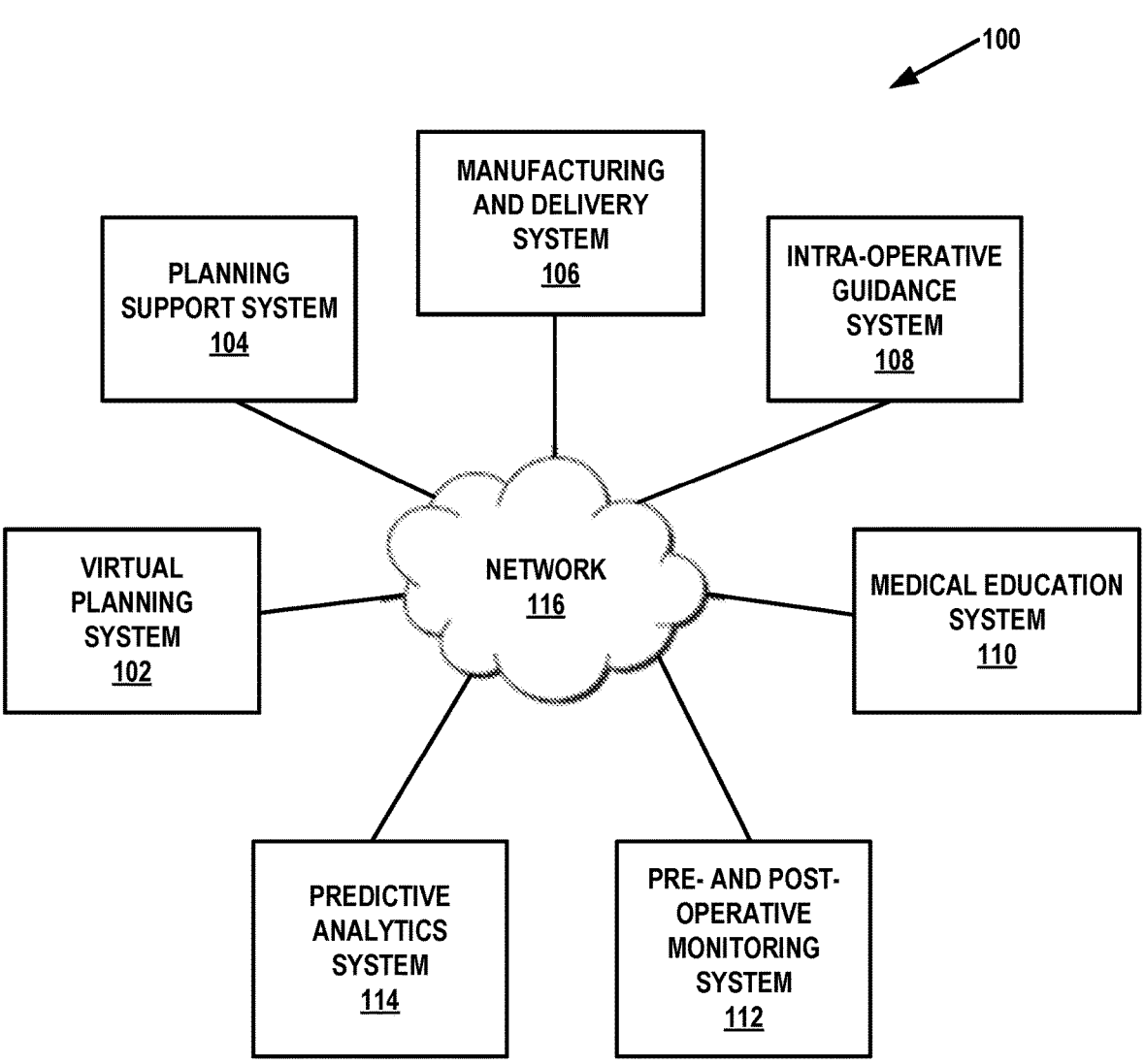
FIG. 1 is a block diagram of an orthopedic surgical system according to an example of this disclosure.

Certain examples of this disclosure are described with reference to the accompanying drawings, wherein like reference numerals denote like elements. It should be understood, however, that the accompanying drawings illustrate only the various implementations described herein and are not meant to limit the scope of various technologies described herein. The drawings show and describe various examples of this disclosure.

In the following description, numerous details are set forth to provide an understanding of the present invention. However, it will be understood by those skilled in the art that the present invention may be practiced without these details and that numerous variations or modifications from the described examples may be possible.

Orthopedic surgery can involve implanting one or more prosthetic devices to repair or replace a patient's damaged or diseased joint. Today, virtual surgical planning tools are available that use image data of the diseased or damaged joint to generate an accurate three-dimensional bone model that can be viewed and manipulated preoperatively by the surgeon. These tools can enhance surgical outcomes by allowing the surgeon to simulate the surgery, select or design an implant that more closely matches the contours of the patient's actual bone, and select or design surgical instruments and guide tools that are adapted specifically for repairing the bone of a particular patient. Use of these planning tools typically results in generation of a preoperative surgical plan, complete with an implant and surgical instruments that are selected or manufactured for the individual patient. Oftentimes, once in the actual operating environment, the surgeon may desire to verify the preoperative surgical plan intraoperatively relative to the patient's actual bone. This verification may result in a determination that an adjustment to the preoperative surgical plan is needed, such as a different implant, a different positioning or orientation of the implant, and/or a different surgical guide for carrying out the surgical plan. In addition, a surgeon may want to view details of the preoperative surgical plan relative to the patient's real bone during the actual procedure in order to more efficiently and accurately position and orient the implant components. For example, the surgeon may want to obtain intra-operative visualization that provides guidance for positioning and orientation of implant components, guidance for preparation of bone or tissue to receive the implant components, guidance for reviewing the details of a procedure or procedural step, and/or guidance for selection of tools or implants and tracking of surgical procedure workflow.

Accordingly, this disclosure describes systems and methods for using a mixed reality (MR) visualization system to assist with creation, implementation, verification, and/or modification of a surgical plan before and during a surgical procedure. Because MR, or in some instances VR, may be used to interact with the surgical plan, this disclosure may also refer to the surgical plan as a "virtual" surgical plan. Visualization tools other than or in addition to mixed reality visualization systems may be used in accordance with techniques of this disclosure. A surgical plan, e.g., as generated by the BLUEPRINT™ system or another surgical planning platform, may include information defining a variety of features of a surgical procedure, such as features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or tissue by the surgeon in bone or tissue preparation steps, and/or positions, axes, planes, angle and/or entry points defining placement of implant components by the surgeon relative to patient bone or tissue. Information such as dimensions, shapes, angles, surface contours, and/or orientations of anatomical features of the patient may be derived from imaging (e.g., x-ray, CT, MRI, ultrasound or other images), direct observation, or other techniques. In some examples, the virtual In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which they are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, hand-held, or otherwise viewable by a user. This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

The Microsoft HOLOLENS™ headset, available from Microsoft Corporation of Redmond, Washington, is an example of a MR device that includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as they exist in the real world. Video games set in imaginary worlds are a common example of VR. The term "VR" also encompasses scenarios where the user is presented with a fully artificial environment in which some virtual object's locations are based on the locations of corresponding physical objects as they relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

These mixed reality systems and methods can be part of an intelligent surgical planning system that includes multiple subsystems that can be used to enhance surgical outcomes. In addition to the preoperative and intraoperative applications discussed above, an intelligent surgical planning system can include postoperative tools to assist with patient recovery and which can provide information that can be used to assist with and plan future surgical revisions or surgical cases for other patients.

Accordingly, systems and methods are also described herein that can be incorporated into an intelligent surgical planning system, such as artificial intelligence systems to assist with planning, implants with embedded sensors (e.g., smart implants) to provide postoperative feedback for use by the healthcare provider and the artificial intelligence system, and mobile applications to monitor and provide information to the patient and the healthcare provider in real-time or near real-time.

Visualization tools are available that utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Technology, Inc. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitor system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (i.e., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing systems configured to operate as a system. In some examples, one or more devices may be shared between the two or more of the subsystems of orthopedic surgical system 100. For instance, in the previous examples, virtual planning system 102 and planning support system 104 may include the same server devices.

In the example of FIG. 1, the devices included in the subsystems of orthopedic surgical system 100 may communicate using communication network 116. Communication network 116 may include various types of communication networks including one or more wide-area networks, such as the Internet, local area networks, and so on. In some examples, communication network 116 may include wired and/or wireless communication links.

Figure 2:
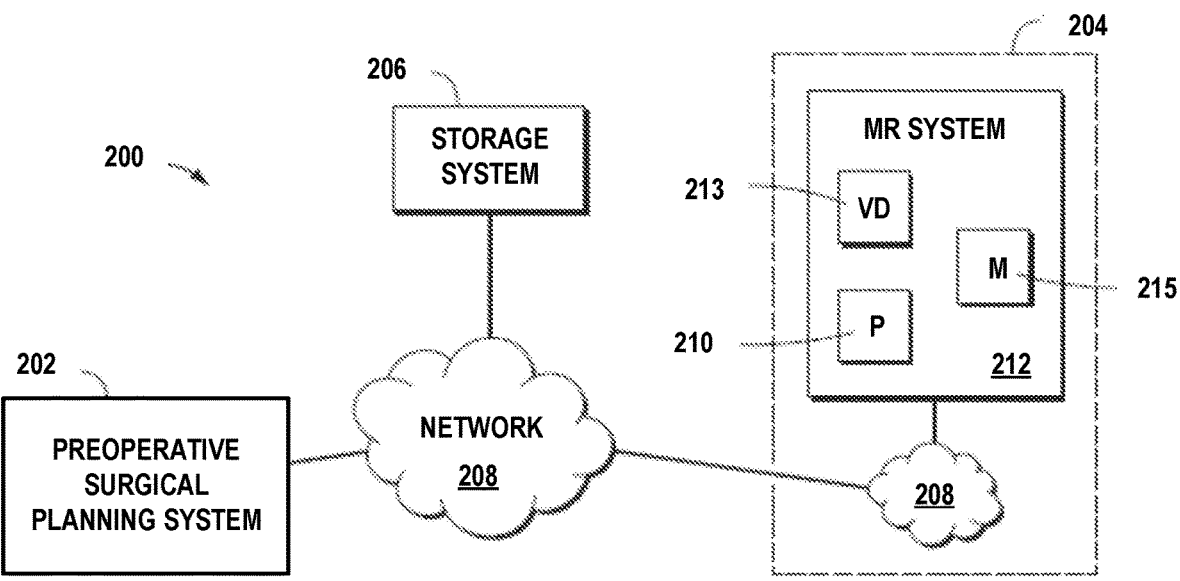
FIG. 2 is a block diagram of an orthopedic surgical system that includes a mixed reality (MR) system, according to an example of this disclosure.

Many variations of orthopedic surgical system 100 are possible in accordance with techniques of this disclosure. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206 and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities that will be described in further detail below. Processing device(s) 210 may also be referred to as processor(s). In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 to present virtual images, such as 3D virtual models, 2D images, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUE-PRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans. For example, medical images of the patient's diseased or damaged bone typically are generated preoperatively in preparation for an orthopedic surgical procedure. The medical images can include images of the relevant bone(s) taken along the sagittal plane and the coronal plane of the patient's body. The medical images can include X-ray images, magnetic resonance imaging (MRI) images, computerized tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intra-operatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

In this way, FIG. 2 illustrates a surgical planning system that includes a preoperative surgical planning system 202 to generate a virtual surgical plan customized to repair an anatomy of interest of a particular patient. For example, the virtual surgical plan may include a plan for an orthopedic joint repair surgical procedure, such as one of a standard total shoulder arthroplasty or a reverse shoulder arthroplasty. In this example, details of the virtual surgical plan may include details relating to at least one of preparation of glenoid bone or preparation of humeral bone. In some examples, the orthopedic joint repair surgical procedure is one of a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, and an augmented glenoid reverse shoulder arthroplasty.

The virtual surgical plan may include a 3D virtual model corresponding to the anatomy of interest of the particular patient and a 3D model of a prosthetic component matched to the particular patient to repair the anatomy of interest or selected to repair the anatomy of interest. Furthermore, in the example of FIG. 2, the surgical planning system includes a storage system 206 to store data corresponding to the virtual surgical plan. The surgical planning system of FIG. 2 also includes MR system 212, which may comprise visualization device 213. In some examples, visualization device 213 is wearable by a user. In some examples, visualization device 213 is held by a user, or rests on a surface in a place accessible to the user. MR system 212 may be configured to present a user interface via visualization device 213. The user interface is visually perceptible to the user using visualization device 213. For instance, in one example, a screen of visualization device 213 may display real-world images and the user interface on a screen. In some examples, visualization device 213 may project virtual, holographic images onto see-through holographic lenses and also permit a user to see real-world objects of a real-world environment through the lenses. In other words, visualization device 213 may comprise one or more see-through holographic lenses and one or more display devices that present imagery to the user via the holographic lenses to present the user interface to the user.

In some examples, visualization device 213 is configured such that the user can manipulate the user interface (which is visually perceptible to the user when the user is wearing or otherwise using visualization device 213) to request and view details of the virtual surgical plan for the particular patient, including a 3D virtual model of the anatomy of interest (e.g., a 3D virtual bone of the anatomy of interest) and a 3D model of the prosthetic component selected to repair an anatomy of interest. In some such examples, visualization device 213 is configured such that the user can manipulate the user interface so that the user can view the virtual surgical plan intraoperatively, including (at least in some examples) the 3D virtual model of the anatomy of interest (e.g., a 3D virtual bone of the anatomy of interest). In some examples, MR system 212 can be operated in an augmented surgery mode in which the user can manipulate the user interface intraoperatively so that the user can visually perceive details of the virtual surgical plan projected in a real environment, e.g., on a real anatomy of interest of the particular patient. In this disclosure, the terms real and real world may be used in a similar manner. For example, MR system 212 may present one or more virtual objects that provide guidance for preparation of a bone surface and placement of a prosthetic implant on the bone surface. Visualization device 213 may present one or more virtual objects in a manner in which the virtual objects appear to be overlaid on an actual, real anatomical object of the patient, within a real-world environment, e.g., by displaying the virtual object(s) with actual, real-world patient anatomy viewed by the user through holographic lenses. For example, the virtual objects may be 3D virtual objects that appear to reside within the real-world environment with the actual, real anatomical object.

Figure 3:
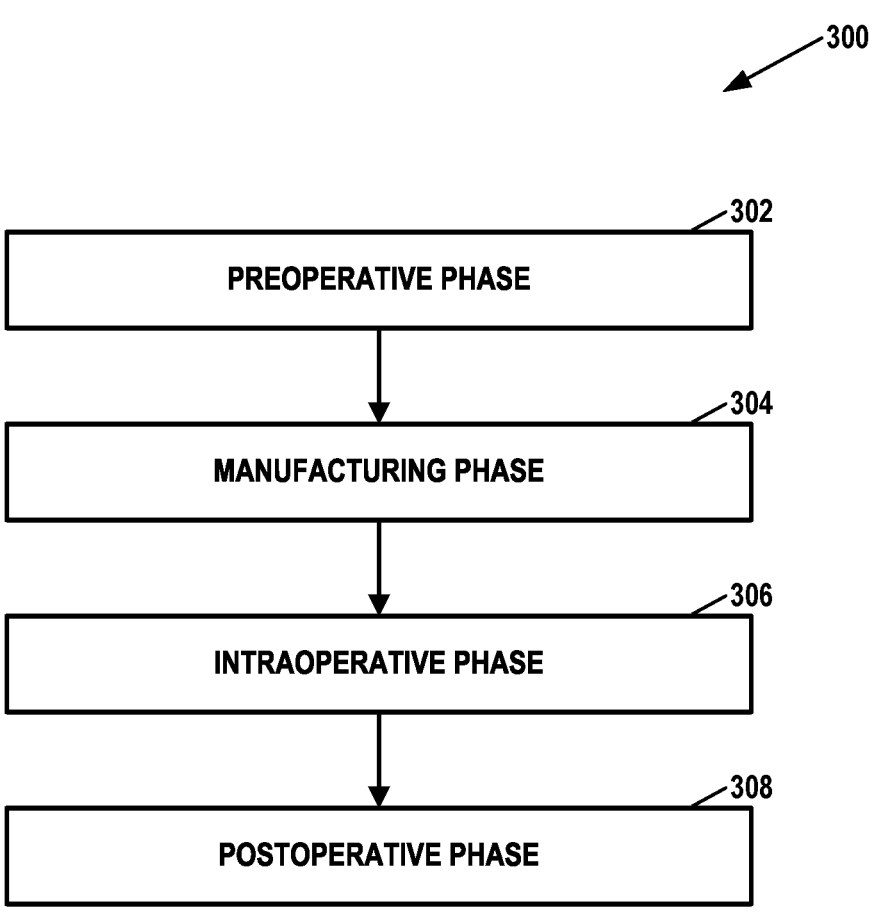
FIG. 3 is a flowchart illustrating example phases of a surgical lifecycle.

FIG. 3 is a flowchart illustrating example phases of a surgical lifecycle 300. In the example of FIG. 3, surgical lifecycle 300 begins with a preoperative phase (302). During the preoperative phase, a surgical plan is developed. The preoperative phase is followed by a manufacturing and delivery phase (304). During the manufacturing and delivery phase, patient-specific items, such as parts and equipment, needed for executing the surgical plan are manufactured and delivered to a surgical site. In some examples, it is unnecessary to manufacture patient-specific items in order to execute the surgical plan. An intraoperative phase follows the manufacturing and delivery phase (306). The surgical plan is executed during the intraoperative phase. In other words, one or more persons perform the surgery on the patient during the intraoperative phase. The intraoperative phase is followed by the postoperative phase (308). The postoperative phase includes activities occurring after the surgical plan is complete. For example, the patient may be monitored during the postoperative phase for complications.

As described in this disclosure, orthopedic surgical system 100 (FIG. 1) may be used in one or more of preoperative phase 302, the manufacturing and delivery phase 304, the intraoperative phase 306, and the postoperative phase 308. For example, virtual planning system 102 and planning support system 104 may be used in preoperative phase 302. Manufacturing and delivery system 106 may be used in the manufacturing and delivery phase 304. Intraoperative guidance system 108 may be used in intraoperative phase 306. Some of the systems of FIG. 1 may be used in multiple phases of FIG. 3. For example, medical education system 110 may be used in one or more of preoperative phase 302, intraoperative phase 306, and postoperative phase 308; pre- and postoperative monitoring system 112 may be used in preoperative phase 302 and postoperative phase 308. Predictive analytics system 114 may be used in preoperative phase 302 and postoperative phase 308. Various workflows may exist within the surgical process of FIG. 3. For example, different workflows within the surgical process of FIG. 3 may be appropriate for different types of surgeries.

As mentioned above, one or more of the subsystems of orthopedic surgical system 100 may include one or more mixed reality (MR) systems, such as MR system 212 (FIG. 2). Each MR system may include a visualization device. For instance, in the example of FIG. 2, MR system 212 includes visualization device 213. In some examples, in addition to including a visualization device, an MR system may include external computing resources that support the operations of the visualization device. For instance, the visualization device of an MR system may be communicatively coupled to a computing device (e.g., a personal computer, backpack computer, smartphone, etc.) that provides the external computing resources. Alternatively, adequate computing resources may be provided on or within visualization device 213 to perform necessary functions of the visualization device.

Figure 4:
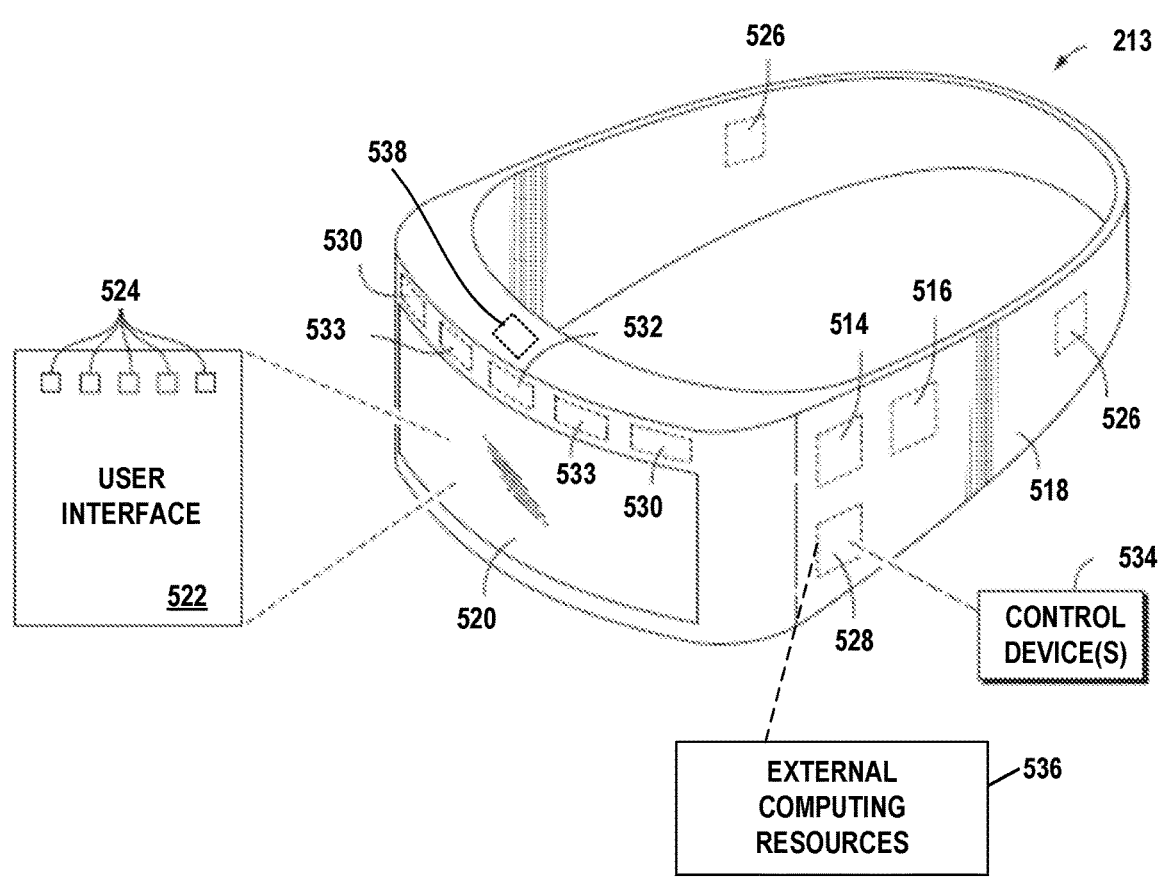
FIG. 4 is a schematic representation of a visualization device for use in a mixed reality (MR) system, according to an example of this disclosure.

FIG. 4 is a schematic representation of visualization device 213 for use in an MR system, such as MR system 212 of FIG. 2, according to an example of this disclosure. As shown in the example of FIG. 4, visualization device 213 can include a variety of electronic components found in a computing system, including one or more processor(s) 514 (e.g., microprocessors or other types of processing units) and memory 516 that may be mounted on or within a frame 518. Furthermore, in the example of FIG. 4, visualization device 213 may include a transparent screen 520 that is positioned at eye level when visualization device 213 is worn by a user. In some examples, screen 520 can include one or more liquid crystal displays (LCDs) or other types of display screens on which images are perceptible to a surgeon who is wearing or otherwise using visualization device 213 via screen 520. Other display examples include organic light emitting diode (OLED) displays. In some examples, visualization device 213 can operate to project 3D images onto the user's retinas using techniques known in the art.

In some examples, screen 520 may include see-through holographic lenses. sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 538 within visualization device 213. In other words, visualization device 213 may include one or more see-through holographic lenses to present virtual images to a user. Hence, in some examples, visualization device 213 can operate to project 3D images onto the user's retinas via screen 520, e.g., formed by holographic lenses. In this manner, visualization device 213 may be configured to present a 3D virtual image to a user within a real-world view observed through screen 520, e.g., such that the virtual image appears to form part of the real-world environment. In some examples, visualization device 213 may be a Microsoft HOLOLENS™ headset, available from Microsoft Corporation, of Redmond, Wash., USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Although the example of FIG. 4 illustrates visualization device 213 as a head-wearable device, visualization device 213 may have other forms and form factors. For instance, in some examples, visualization device 213 may be a handheld smartphone or tablet.

Visualization device 213 can also generate a user interface (UI) 522 that is visible to the user, e.g., as holographic imagery projected into see-through holographic lenses as described above. For example, UI 522 can include a variety of selectable widgets 524 that allow the user to interact with a mixed reality (MR) system, such as MR system 212 of FIG. 2. Imagery presented by visualization device 213 may include, for example, one or more 3D virtual objects. Details of an example of UI 522 are described elsewhere in this disclosure. Visualization device 213 also can include a speaker or other sensory devices 526 that may be positioned adjacent the user's ears. Sensory devices 526 can convey audible information or other perceptible information (e.g., vibrations) to assist the user of visualization device 213.

Visualization device 213 can also include a transceiver 528 to connect visualization device 213 to a processing device 510 and/or to network 208 and/or to a computing cloud, such as via a wired communication protocol or a wireless protocol, e.g., Wi-Fi, Bluetooth, etc. Visualization device 213 also includes a variety of sensors to collect sensor data, such as one or more optical camera(s) 530 (or other optical sensors) and one or more depth camera(s) 532 (or other depth sensors), mounted to, on or within frame 518. In some examples, the optical sensor(s) 530 are operable to scan the geometry of the physical environment in which user of MR system 212 is located (e.g., an operating room) and collect two-dimensional (2D) optical image data (either monochrome or color). Depth sensor(s) 532 are operable to provide 3D image data, such as by employing time of flight, stereo or other known or future-developed techniques for determining depth and thereby generating image data in three dimensions. Other sensors can include motion sensors 533 (e.g., Inertial Mass Unit (IMU) sensors, accelerometers, etc.) to assist with tracking movement.

MR system 212 processes the sensor data so that geometric, environmental, textural, etc. landmarks (e.g., corners, edges or other lines, walls, floors, objects) in the user's environment or "scene" can be defined and movements within the scene can be detected. As an example, the various types of sensor data can be combined or fused so that the user of visualization device 213 can perceive 3D images that can be positioned, or fixed and/or moved within the scene. When fixed in the scene, the user can walk around the 3D image, view the 3D image from different perspectives, and manipulate the 3D image within the scene using hand gestures, voice commands, gaze line (or direction) and/or other control inputs. As another example, the sensor data can be processed so that the user can position a 3D virtual object (e.g., a bone model) on an observed physical object in the scene (e.g., a surface, the patient's real bone, etc.) and/or orient the 3D virtual object with other virtual images displayed in the scene. As yet another example, the sensor data can be processed so that the user can position and fix a virtual representation of the surgical plan (or other widget, image or information) onto a surface, such as a wall of the operating room. Yet further, the sensor data can be used to recognize surgical instruments and the position and/or location of those instruments.

Visualization device 213 may include one or more processors 514 and memory 516, e.g., within frame 518 of the visualization device. In some examples, one or more external computing resources 536 process and store information, such as sensor data, instead of or in addition to in-frame processor(s) 514 and memory 516. In this way, data processing and storage may be performed by one or more processors 514 and memory 516 within visualization device 213 and/or some of the processing and storage requirements may be offloaded from visualization device 213. Hence, in some examples, one or more processors that control the operation of visualization device 213 may be within the visualization device, e.g., as processor(s) 514. Alternatively, in some examples, at least one of the processors that controls the operation of visualization device 213 may be external to the visualization device, e.g., as processor(s) 210. Likewise, operation of visualization device 213 may, in some examples, be controlled in part by a combination one or more processors 514 within the visualization device and one or more processors 210 external to the visualization device.

For instance, in some examples, when visualization device 213 is in the context of FIG. 2, processing of the sensor data can be performed by processing device(s) 210 in conjunction with memory or storage device(s) (M) 215. In some examples, processor(s) 514 and memory 516 mounted to frame 518 may provide sufficient computing resources to process the sensor data collected by cameras 530, 532 and motion sensors 533. In some examples, the sensor data can be processed using a Simultaneous Localization and Mapping (SLAM) algorithm, or other known or future-developed algorithm for processing and mapping 2D and 3D image data and tracking the position of visualization device 213 in the 3D scene. In some examples, image tracking may be performed using sensor processing and tracking functionality provided by the Microsoft HOLOLENS™ system, e.g., by one or more sensors and processors 514 within a visualization device 213 substantially conforming to the Microsoft HOLOLENS™ device or a similar mixed reality (MR) visualization device.

In some examples, MR system 212 can also include user-operated control device(s) 534 that allow the user to operate MR system 212, use MR system 212 in spectator mode (either as master or observer), interact with UI 522 and/or otherwise provide commands or requests to processing device(s) 210 or other systems connected to network 208. As examples, the control device(s) 234 can include a microphone, a touch pad, a control panel, a motion sensor or other types of control input devices with which the user can interact.

Figure 5:
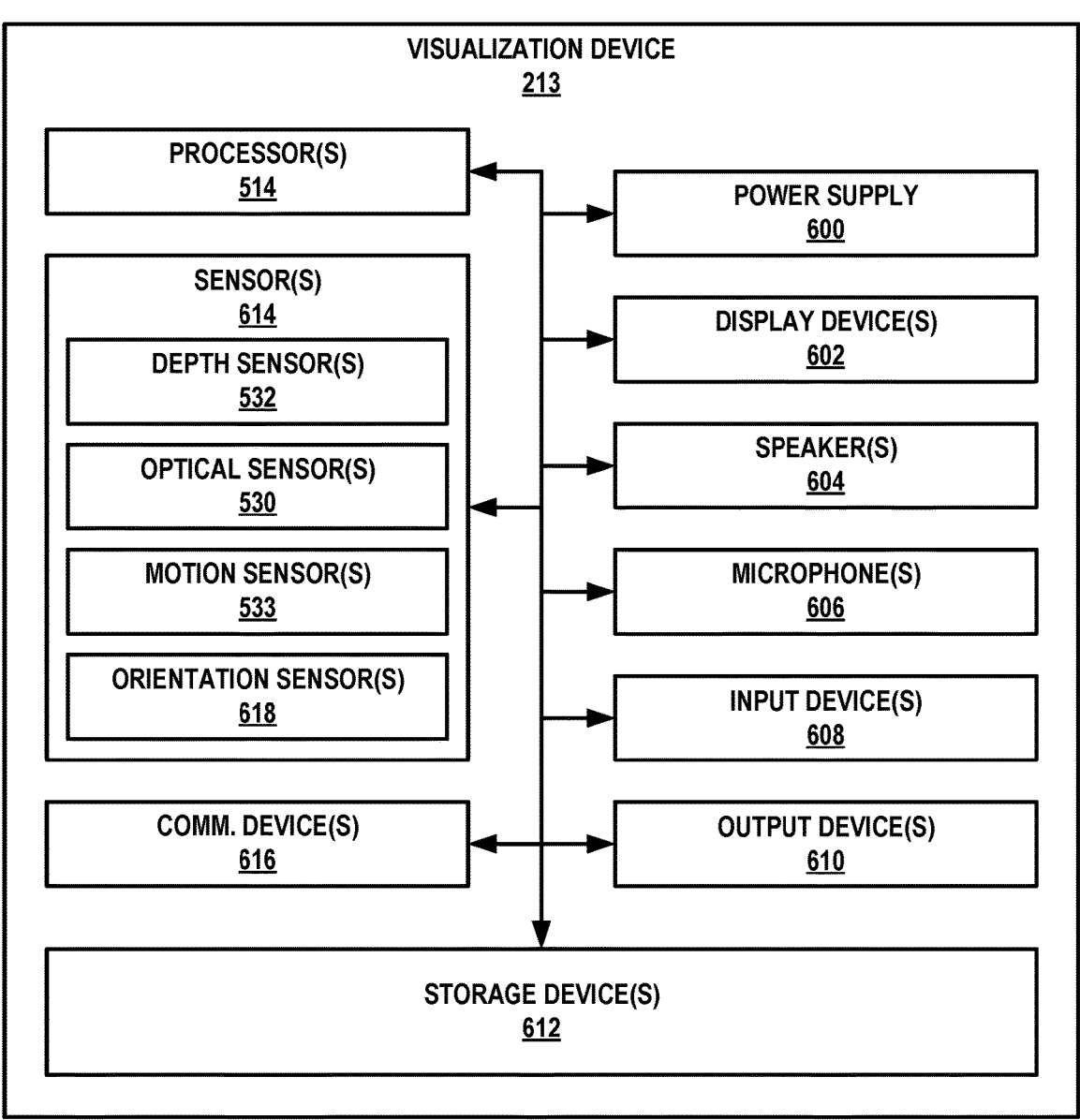
FIG. 5 is a block diagram illustrating example components of a visualization device for use in a mixed reality (MR) system, according to an example of this disclosure.
Figure 6:
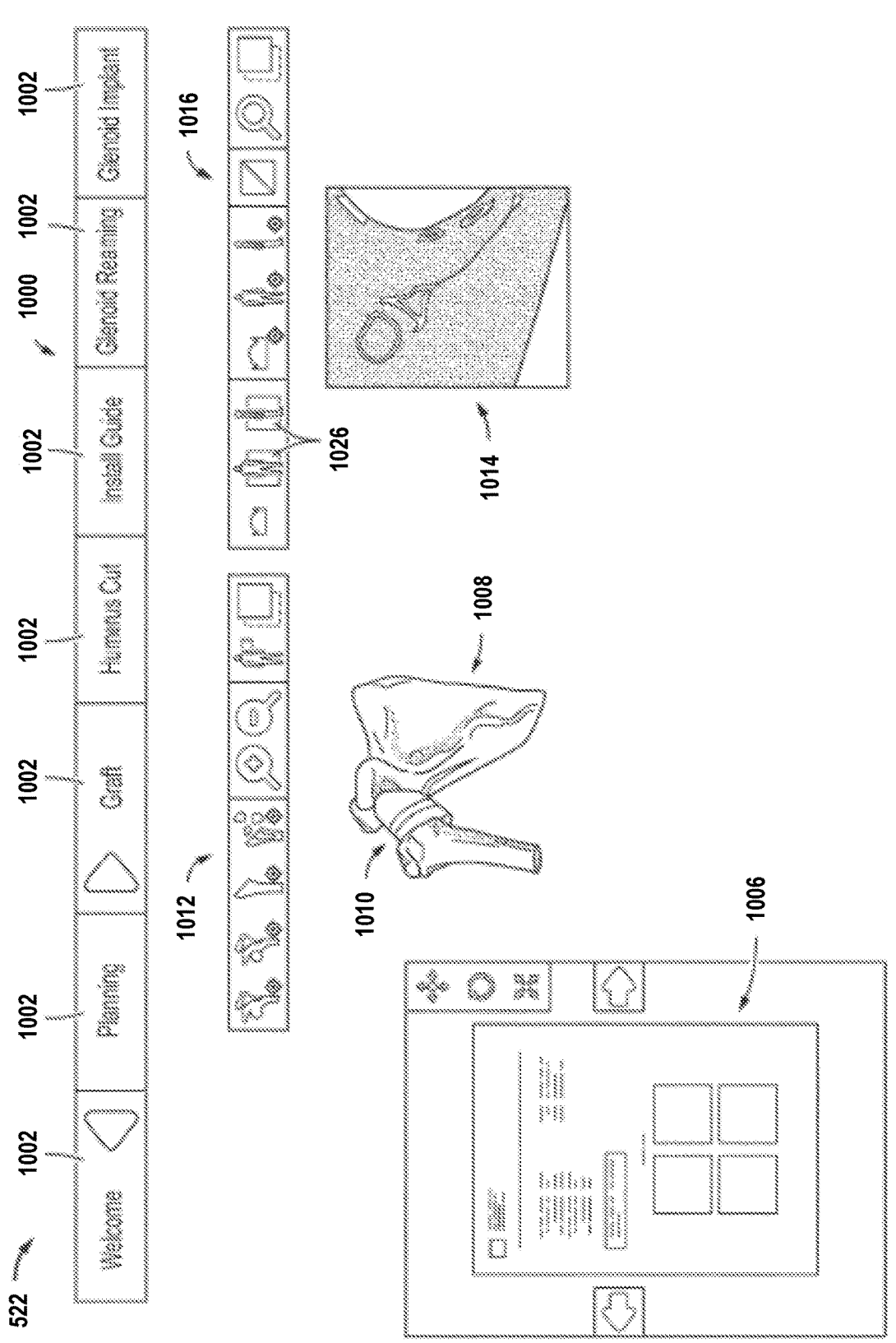
FIG. 6 illustrates an example of a page of a user interface of a mixed reality (MR) system, according to an example of this disclosure.
Figure 7:
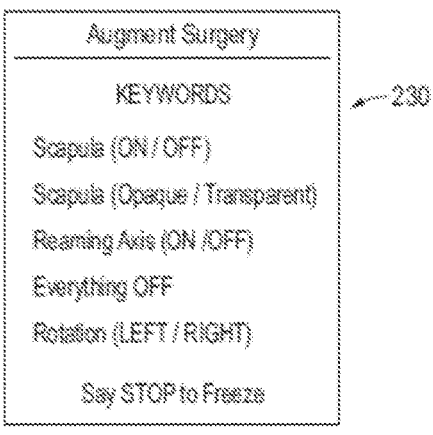
FIG. 7 is an example of an Augment Surgery mode widget that is displayed on various pages of the user interface of FIG. 6, according to an example of this disclosure.

FIG. 5 is a block diagram illustrating example components of visualization device 213 for use in a MR system. In the example of FIG. 5, visualization device 213 includes processors 514, a power supply 600, display device(s) 602, speakers 604, microphone(s) 606, input device(s) 608, output device(s) 610, storage device(s) 612, sensor(s) 614, and communication devices 616. In the example of FIG. 6, sensor(s) 616 may include depth sensor(s) 532, optical sensor(s) 530, motion sensor(s) 533, and orientation sensor (s) 618. Optical sensor(s) 530 may include cameras, such as Red-Green-Blue (RGB) video cameras, infrared cameras, or other types of sensors that form images from light. Display device(s) 602 may display imagery to present a user interface to the user.

Speakers 604, in some examples, may form part of sensory devices 526 shown in FIG. 4. In some examples, display devices 602 may include screen 520 shown in FIG. 4. For example, as discussed with reference to FIG. 4, display device(s) 602 may include see-through holographic lenses, in combination with projectors, that permit a user to see real-world objects, in a real-world environment, through the lenses, and also see virtual 3D holographic imagery projected into the lenses and onto the user's retinas, e.g., by a holographic projection system. In this example, virtual 3D holographic objects may appear to be placed within the real-world environment. In some examples, display devices 602 include one or more display screens, such as LCD display screens, OLED display screens, and so on. The user interface may present virtual images of details of the virtual surgical plan for a particular patient.

In some examples, a user may interact with and control visualization device 213 in a variety of ways. For example, microphones 606, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, one or more cameras or other optical sensors 530 of sensors 614 may detect and interpret gestures to perform operations as described above. As a further example, sensors 614 may sense gaze direction and perform various operations as described elsewhere in this disclosure. In some examples, input devices 608 may receive manual input from a user, e.g., via a handheld controller including one or more buttons, a keypad, a touchscreen, joystick, trackball, and/or other manual input media, and perform, in response to the manual user input, various operations as described above.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

FIG. 6 illustrates an example of a page of a user interface of a mixed reality system, according to an example of this disclosure, e.g. as produced for a particular patient's surgical plan. Using visualization device 213, a user can perceive and interact with UI 522. In the example shown in FIG. 6, UI 522 includes a workflow bar 1000 with selectable buttons 1002 that represent a surgical workflow, spanning various surgical procedure steps for operations on the humerus and glenoid in a shoulder arthroplasty procedure. Selection of a button 1002 can lead to display of various selectable widgets with which the user can interact, such as by using hand gestures, voice commands, gaze direction, connected lens and/or other control inputs. Selection of widgets can launch various modes of operation of MR system 212, display information or images generated by MR system 212, allow the user to further control and/or manipulate the information and images, lead to further selectable menus or widgets, etc.

The user can also organize or customize UI 522 by manipulating, moving and orienting any of the displayed widgets according to the user's preferences, such as by visualization device 213 or other device detecting gaze direction, hand gestures and/or voice commands. Further, the location of widgets that are displayed to the user can be fixed relative to the scene. Thus, as the user's gaze (i.e., eye direction) moves to view other features of the user interface 522, other virtual images, and/or real objects physically present in the scene (e.g., the patient, an instrument set, etc.), the widgets may remain stationary and do not interfere with the user's view of the other features and objects. As yet another example, the user can control the opacity or transparency of the widgets or any other displayed images or information. The user also can navigate in any direction between the buttons 1002 on the workflow bar 1000 and can select any button 1002 at any time during use of MR system 212. Selection and manipulation of widgets, information, images or other displayed features can be implemented based on visualization device 213 or other device detecting user gaze direction, hand motions, voice commands or any combinations thereof.

In the example of FIG. 6, UI 522 is configured for use in shoulder repair procedures and includes, as examples, buttons 1002 on workflow bar 1000 that correspond to a "Welcome" page, a "Planning" page, a "Graft" page, a "Humerus Cut" page, an "Install Guide" page, a "Glenoid Reaming" page, and a "Glenoid Implant" page. The presentation of the "Install Guide" page may be optional as, in some examples, glenoid reaming may be accomplished using virtual guidance and without the application of a glenoid guide.

As shown FIG. 6, the "Planning" page in this example of UI 522 displays various information and images corresponding to the selected surgical plan, including an image 1006 of a surgical plan file (e.g., a pdf file or other appropriate media format) that corresponds to the selected plan (including preoperative and postoperative information); a 3D virtual bone model 1008 and a 3D virtual implant model 1010 along with a 3D image navigation bar 1012 for manipulating the 3D virtual models 1008, 1010 (which may be referred to as 3D images); a viewer 1014 and a viewer navigation bar 1016 for viewing a multi-planar view associated with the selected surgical plan. MR system 212 may present the "Planning" page as a virtual MR object to the user during preoperative phase 302 (FIG. 3). For instance, MR system 212 may present the "Planning" page to the user to help the user classify a pathology, select a surgical plan, tailor the surgical plan to the patient, revise the surgical plan, and review the surgical plan.

The surgical plan image 1006 may be a compilation of preoperative (and, optionally, postoperative) patient information and the surgical plan for the patient that are stored in a database in storage system 206. In some examples, surgical plan image 1006 can correspond to a multi-page document through which the user can browse. For example, further images of pages can display patient information, information regarding the anatomy of interest, postoperative measurements, and various 2D images of the anatomy of interest. Yet further page images can include, as examples, planning information associated with an implant selected for the patient, such as anatomy measurements and implant size, type and dimensions; planar images of the anatomy of interest; images of a 3D model showing the positioning and orientation of a surgical guide selected for the patient to assist with execution of the surgical plan; etc.

It should be understood that the surgical plan image 1006 can be displayed in any suitable format and arrangement and that other implementations of the systems and techniques described herein can include different information depending upon the needs of the application in which the plan image 1006 is used.

Referring again FIG. 6, the Planning page of UI 522 also may provide images of the 3D virtual bone model 1008 and the 3D model of the implant components 1010 along with navigation bar 1012 for manipulating 3D virtual models 1008, 1010. For example, selection or de-selection of the icons on navigation bar 1012 allow the user to selectively view different portions of 3D virtual bone model 1008 with or without the various implant components 1010. For example, the scapula of virtual bone model 1008 and the glenoid implant of implant model 1010 have been de-selected, leaving only the humerus bone and the humeral implant components visible. Other icons can allow the user to zoom in or out, and the user also can rotate and re-orient 3D virtual models 1008, 1010, e.g., using gaze detection, hand gestures and/or voice commands.

The Planning page of UI 522 also provides images of 3D virtual bone model 1008 and the 3D model of the implant components 1010 along with navigation bar 1012 for manipulating 3D virtual models 1008, 1010. The Planning page presented by visualization device 213 also includes multi-planar image viewer 1014 (e.g., a DICOM viewer) and navigation bar 1016 that allow the user to view patient image data and to switch between displayed slices and orientations. For example, the user can select 2D Planes icons 1026 on navigation bar 1016 so that the user can view the 2D sagittal and coronal planes of the patient's body in multi-planar image viewer 1014.

Workflow bar 1000 in FIG. 6 includes further pages that correspond to steps in the surgical workflow for a particular orthopedic procedure (here, a shoulder repair procedure). In the example of FIG. 6, workflow bar 1000 includes elements labeled "Graft," "Humerus Cut," "Install Guide," "Glenoid Reaming," and "Glenoid Implant" that correspond to workflow pages for steps in the surgical workflow for a shoulder repair procedure. In general, these workflow pages include information that can be useful for a health care professional during planning of or during performance of the surgical procedure, and the information presented upon selection of these pages is selected and organized in a manner that is intended to minimize disturbances or distractions to the surgeon during a procedure. Thus, the amount of displayed information is optimized and the utility of the displayed information is maximized. These workflow pages may be used as part of intraoperative phase 306 (FIG. 3) to guide a surgeon, nurse or other medical technician through the steps in a surgical procedure. In some examples, these workflow pages may be used as part of preoperative phase 302 (FIG. 3) to enable a user to visualize 3-dimensional models of objects involved in various steps of a surgical workflow.

In the example shown, each workflow page that can be selected by the user (e.g., a surgeon) can include an Augment Surgery widget, such as Augment Surgery widget 230 (shown in FIG. 11), that, when selected, launches an operational mode of MR system 212 in which a user using (e.g., wearing) visualization device 213 (FIG. 2) can see the details (e.g., virtual images of details) of the surgical plan projected and matched onto the patient bone and use the plan intraoperatively to assist with the surgical procedure. In general, the Augment Surgery mode allows the surgeon to register the virtual 3D model of the patient's anatomy of interest (e.g., glenoid) with the observed real anatomy so that the surgeon can use the virtual surgical planning to assist with implementation of the real surgical procedure, as will be explained in further detail below. There may be different Augment Surgery widgets for each of the steps of the surgery that the surgeon uses during actual surgery. The Augment Surgery widgets for different steps may include different text, control, icons, graphics, etc.

In this example of a shoulder repair procedure, and with reference FIG. 6, the workflow pages of UI 522 that can be used by the surgeon include "Graft", "Humerus Cut", "Install Guide", "Glenoid Reaming", and "Glenoid Implant". The "Graft" step and "Install Guide" steps may be optional. For example, it may not be necessary to take a graft in every procedure and the use of a glenoid reaming guide may not be necessary if MR reaming axis guidance is presented to the user by visualization device 213. A user may view the workflow pages during the preoperative phase 302, during the intraoperative phase 306, or at other times. It may be helpful to a surgeon to view the workflow pages during the preoperative phase 302 in order to tailor a surgical plan for the patient, to review the steps of a surgical plan, or perform other tasks. It may be helpful to a surgeon to view the workflow pages in the intraoperative phase 306 to refresh the surgeon on the anatomy of the patient involved in the corresponding surgical steps, to obtain information on how to perform certain actions during the corresponding surgical steps, to take inventory of surgical instruments, implants or other surgical items needed in the surgical steps, and so on. As mentioned, each of the workflow pages generally corresponds to a step in the workflow for the particular surgical procedure. Thus, for example, the Graft page allows the user to visualize a bone graft matched for a particular patient and provides the user with sufficient information for selecting, designing and/or modifying the shape and dimensions of bone graft 232, if desired. As an example, bone graft 232 may be a bone graft taken from the humerus or another bone.

It should be understood that the workflow pages illustrated and described herein are examples and that UI 522 can include fewer, more, or different pages. For example, in applications of MR system 212 for procedures involving other patient anatomies, such as the ankle, foot, knee, hip or elbow, UI 522 can include pages corresponding to the particular steps specific to the surgical workflow for those procedures.

The images displayed on UI 522 of MR system 212 can be viewed outside or within the surgical operating environment and, in spectator mode, can be viewed by multiple users outside and within the operating environment at the same time. In some circumstances, such as in the operating environment, the surgeon may find it useful to use a control device 534 to direct visualization device 213 such that certain information should be locked into position on a wall or other surface of the operating room, as an example, so that the information does not impede the surgeon's view during the procedure. For example, relevant surgical steps of the surgical plan can be selectively displayed and used by the surgeon or other care providers to guide the surgical procedure.

In various some examples, the display of surgical steps can be automatically controlled so that only the relevant steps are displayed at the appropriate times during the surgical procedure.

As discussed above, surgical lifecycle 300 may include an intraoperative phase 306 during which a surgical operation is performed. One or more users may use orthopedic surgical system 100 in intraoperative phase 306.

Figure 8:
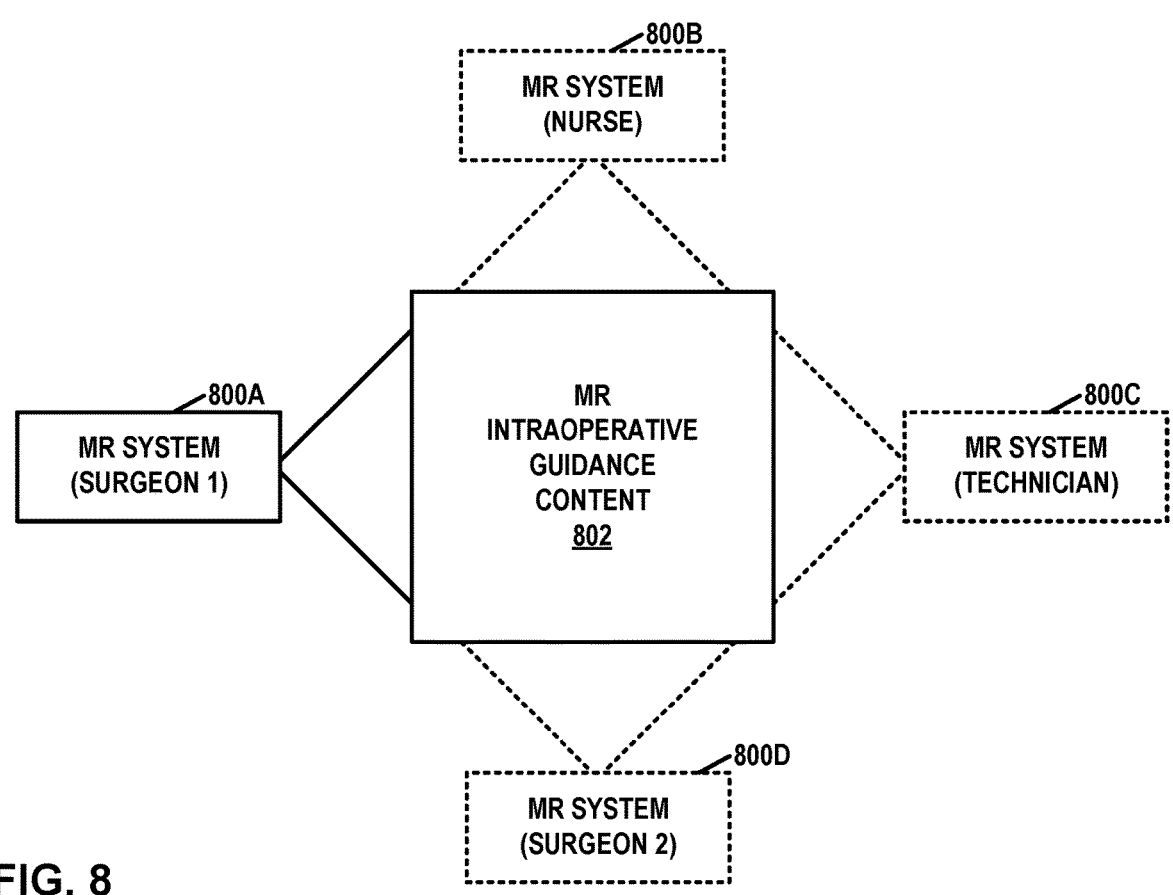
FIG. 8 is a conceptual diagram illustrating an example setting in which a set of users use MR systems of an orthopedic surgical system during an intraoperative phase.

FIG. 8 is a conceptual diagram illustrating an example setting in which a set of one or more users use MR systems of orthopedic surgical system 100 during intraoperative phase 306. In the example of FIG. 8, a surgeon may wear a visualization device (e.g., visualization device 213) of a first MR system 800A (e.g., MR system 212). The visualization device of MR system 800A may present MR intraoperative guidance content 802 to the surgeon during intraoperative phase 306. As described in detail elsewhere in this disclosure, MR intraoperative guidance content 802 may help the surgeon perform for a surgical operation.

Additionally, in the example of FIG. 8, one or more other users may use visualization devices of MR systems of orthopedic surgical system 100 to view MR intraoperative guidance content 802. For example, a nurse may use a visualization device of an MR system 800B of orthopedic surgical system 100. Furthermore, in the example of FIG. 8, a technician may use a visualization device of an MR system 800C of orthopedic surgical system 100. In the example of FIG. 8, a second surgeon may use a visualization device of an MR system 800D of orthopedic surgical system 100. MR systems 800A, 800B, 800C, and 800D may be referred to herein collectively as "MR systems 800." In some examples, a television or other display device may present the view of the surgeon, which may include virtual objects, to one or more other individuals, such as a nurse, surgeon, or technician.

Two or more of the individuals described above (e.g., the first surgeon, the nurse, the technician, the second surgeon) may view the same or different MR intraoperative guidance content 802 at the same time. In examples where two or more of the individuals are viewing the same MR intraoperative guidance content 802 at the same time, the two or more individuals may concurrently view the same MR intraoperative guidance content 802 from the same or different perspectives.

One or more users may use orthopedic surgical system 100 in an intraoperative setting. For example, the users may manipulate a user interface presented by MR systems 800 so that the users can view a virtual surgical plan intraoperatively. For instance, in this example, the users may view a 3D virtual model of an anatomy of interest (e.g., a 3-dimensional virtual bone model of an anatomy of interest).

Figure 9:
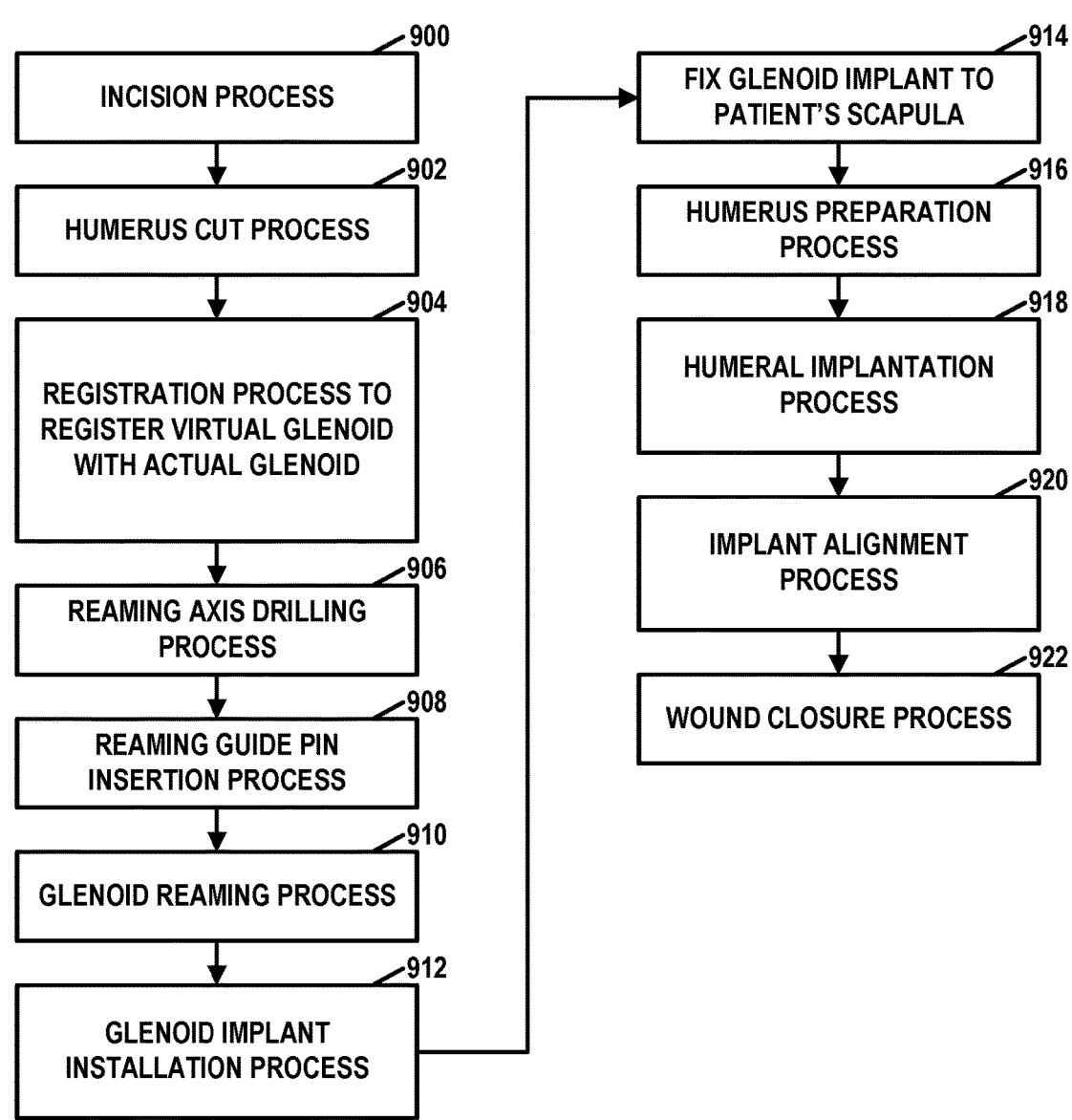
FIG. 9 is a flowchart illustrating example stages of a shoulder joint repair surgery.

In some examples, one or more users, including at least one surgeon, may use orthopedic surgical system 100 in an intraoperative setting to perform shoulder surgery. FIG. 9 is a flowchart illustrating example stages of a shoulder joint repair surgery. As discussed above, FIG. 9 describes an example surgical process for a shoulder surgery. The surgeon may wear or otherwise use visualization device 213 during each step of the surgical process of FIG. 9. In other examples, a shoulder surgery may include more, fewer, or different steps. For example, a shoulder surgery may include step for adding a bone graft, adding cement, and/or other steps. In some examples, visualization device 213 may present virtual guidance to guide the surgeon, nurse, or other users, through the steps in the surgical workflow.

In the example of FIG. 9, a surgeon performs an incision process (900). During the incision process, the surgeon makes a series of incisions to expose a patient's shoulder joint. In some examples, an MR system (e.g., MR system 212, MR system 800A, etc.) may help the surgeon perform the incision process, e.g., by displaying virtual guidance imagery illustrating how to where to make the incision.

Furthermore, in the example of FIG. 9, the surgeon may perform a humerus cut process (902). During the humerus cut process, the surgeon may remove a portion of the humeral head of the patient's humerus. Removing the portion of the humeral head may allow the surgeon to access the patient's glenoid. Additionally, removing the portion of the humeral head may allow the surgeon to subsequently replace the portion of the humeral head with a humeral implant compatible with a glenoid implant that the surgeon plans to implant in the patient's glenoid.

As discussed above, the humerus preparation process may enable the surgeon to access the patient's glenoid. In the example of FIG. 9, after performing the humerus preparation process, the surgeon may perform a registration process that registers a virtual glenoid object with the patient's actual glenoid bone (904) in the field of view presented to the surgeon by visualization device 213.

After performing the registration process, the surgeon may perform a reaming axis drilling process (906). During the reaming axis drilling process, the surgeon may drill a reaming axis guide pin hole in the patient's glenoid to receive a reaming guide pin. In some examples, at a later stage of the shoulder surgery, the surgeon may insert a reaming axis pin into the reaming axis guide pin hole. In some examples, an MR system (e.g., MR system 212, MR system 800A, etc.) may present a virtual reaming axis to help the surgeon perform the drilling in alignment with the reaming axis and thereby place the reaming guide pin in the correct location and with the correct orientation.

The surgeon may perform the reaming axis drilling process in one of various ways. For example, the surgeon may perform a guide-based process to drill the reaming axis pin hole. In the case, a physical guide is placed on the glenoid to guide drilling of the reaming axis pin hole. In other examples, the surgeon may perform a guide-free process, e.g., with presentation of a virtual reaming axis that guides the surgeon to drill the reaming axis pin hole with proper alignment. An MR system (e.g., MR system 212, MR system 800A, etc.) may help the surgeon perform either of these processes to drill the reaming axis pin hole.

Figure 19:
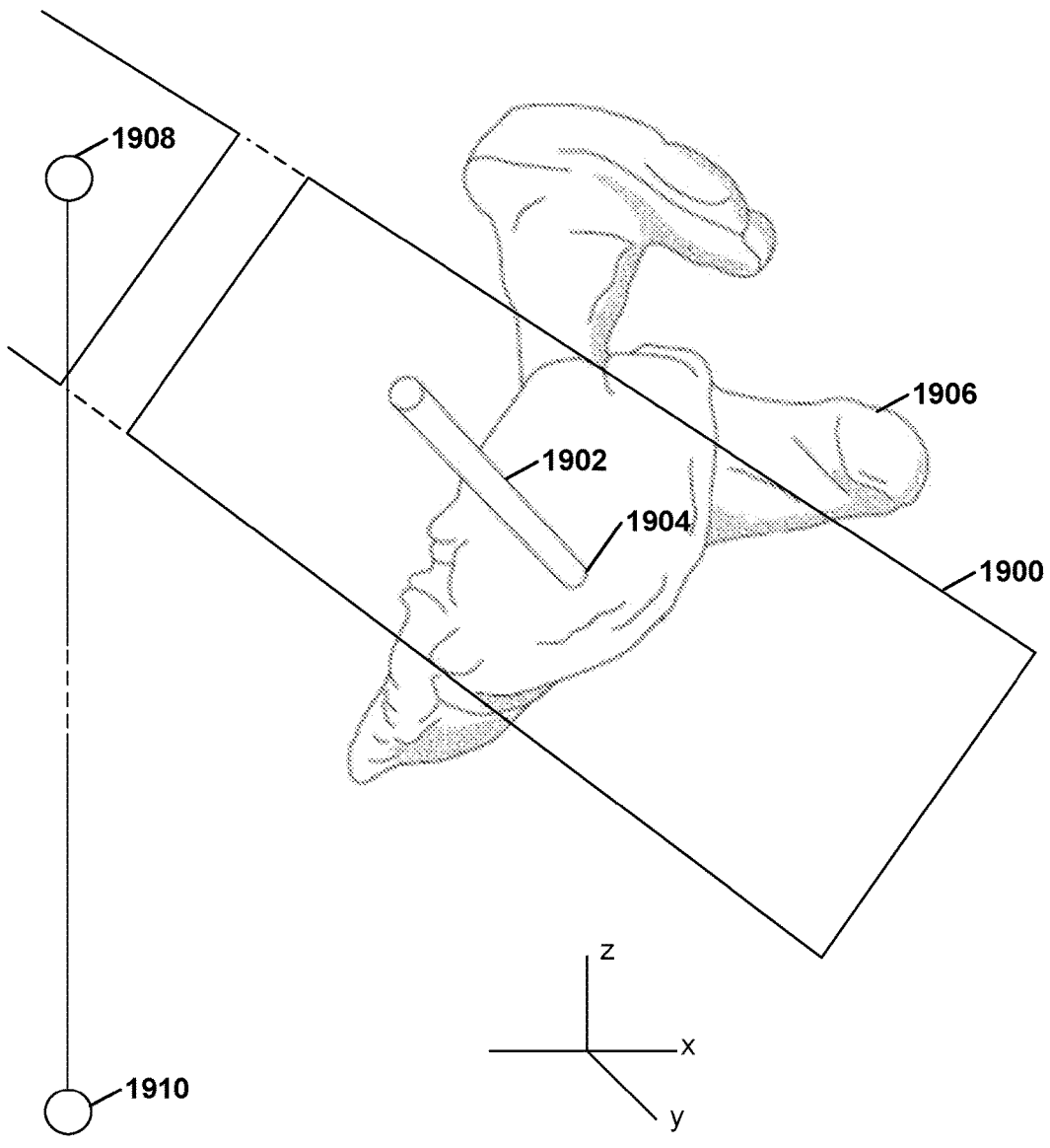
FIG. 19 is a conceptual diagram illustrating an example technique for determining a location for a user to stand within an operating room, in accordance with a technique of this disclosure.

Furthermore, in the surgical process of FIG. 19, the surgeon may perform a reaming axis pin insertion process (908). During the reaming axis pin insertion process, the surgeon inserts a reaming axis pin into the reaming axis pin hole drilled into the patient's scapula. In some examples, an MR system (e.g., MR system 212, MR system 800A, etc.) may present virtual guidance information to help the surgeon perform the reaming axis pin insertion process. In some examples, the reaming axis pin itself is used to drill the reaming axis pin hole and there is not need to for a separate step of inserting the reaming axis pin after drilling the reaming axis pin hole.

After performing the reaming axis insertion process, the surgeon may perform a glenoid reaming process (910). During the glenoid reaming process, the surgeon reams the patient's glenoid. Reaming the patient's glenoid may result in an appropriate surface for installation of a glenoid implant. In some examples, to ream the patient's glenoid, the surgeon may affix a reaming bit to a surgical drill. The reaming bit defines an axial cavity along an axis of rotation of the reaming bit. The axial cavity has an inner diameter corresponding to an outer diameter of the reaming axis pin.

After affixing the reaming bit to the surgical drill, the surgeon may position the reaming bit so that the reaming axis pin is in the axial cavity of the reaming bit. Thus, during the glenoid reaming process, the reaming bit may spin around the reaming axis pin. In this way, the reaming axis pin may prevent the reaming bit from wandering during the glenoid reaming process. In some examples, multiple tools may be used to ream the patient's glenoid. An MR system (e.g., MR system 212, MR system 800A, etc.) may present virtual guidance to help the surgeon or other users to perform the glenoid reaming process. For example, the MR system may help a user, such as the surgeon, select a reaming bit to use in the glenoid reaming process. In some examples, the MR system present virtual guidance to help the surgeon control the depth to which the surgeon reams the user's glenoid. In some examples, the glenoid reaming process includes a paleo reaming step and a neo reaming step to ream different parts of the patient's glenoid.

Additionally, in the surgical process of FIG. 9, the surgeon may perform a glenoid implant installation process (912). During the glenoid implant installation process, the surgeon installs a glenoid implant in the patient's glenoid. In some instances, when the surgeon is performing an anatomical shoulder arthroplasty, the glenoid implant has a concave surface that acts as a replacement for the user's natural glenoid. In other instances, when the surgeon is performing a reverse shoulder arthroplasty, the glenoid implant has a convex surface that acts as a replacement for the user's natural humeral head. In this reverse shoulder arthroplasty, the surgeon may install a humeral implant that has a concave surface that slides over the convex surface of the glenoid implant. As in the other steps of the shoulder surgery of FIG. 9, an MR system (e.g., MR system 212, MR system 800A, etc.) may present virtual guidance to help the surgeon perform the glenoid installation process.

In some examples, the glenoid implantation process includes a process to fix the glenoid implant to the patient's scapula (914). In some examples, the process to fix the glenoid implant to the patient's scapula includes drilling one or more anchor holes or one or more screw holes into the patient's scapula and positioning an anchor such as one or more pegs or a keel of the implant in the anchor hole(s) and/or inserting screws through the glenoid implant and the screw holes, possibly with the use of cement or other adhesive. An MR system (e.g., MR system 212, MR system 800A, etc.) may present virtual guidance to help the surgeon with the process of fixing the glenoid implant the glenoid bone, e.g., including virtual guidance indicating anchor or screw holes to be drilled or otherwise formed in the glenoid, and the placement of anchors or screws in the holes.

Furthermore, in the example of FIG. 9, the surgeon may perform a humerus preparation process (916). During the humerus preparation process, the surgeon prepares the humerus for the installation of a humerus implant. In instances where the surgeon is performing an anatomical shoulder arthroplasty, the humerus implant may have a convex surface that acts as a replacement for the patient's natural humeral head. The convex surface of the humerus implant slides within the concave surface of the glenoid implant. In instances where the surgeon is performing a reverse shoulder arthroplasty, the humerus implant may have a concave surface and the glenoid implant has a corresponding convex surface. As described elsewhere in this disclosure, an MR system (e.g., MR system 212, MR system 800A, etc.) may present virtual guidance information to help the surgeon perform the humerus preparation process.

Furthermore, in the example surgical process of FIG. 9, the surgeon may perform a humerus implant installation process (918). During the humerus implant installation process, the surgeon installs a humerus implant on the patient's humerus. As described elsewhere in this disclosure, an MR system (e.g., MR system 212, MR system 800A, etc.) may present virtual guidance to help the surgeon perform the humerus preparation process.

After performing the humerus implant installation process, the surgeon may perform an implant alignment process that aligns the installed glenoid implant and the installed humerus implant (920). For example, in instances where the surgeon is performing an anatomical shoulder arthroplasty, the surgeon may nest the convex surface of the humerus implant into the concave surface of the glenoid implant. In instances where the surgeon is performing a reverse shoulder arthroplasty, the surgeon may nest the convex surface of the glenoid implant into the concave surface of the humerus implant. Subsequently, the surgeon may perform a wound closure process (922). During the wound closure process, the surgeon may reconnect tissues severed during the incision process in order to close the wound in the patient's shoulder.

Figure 10:
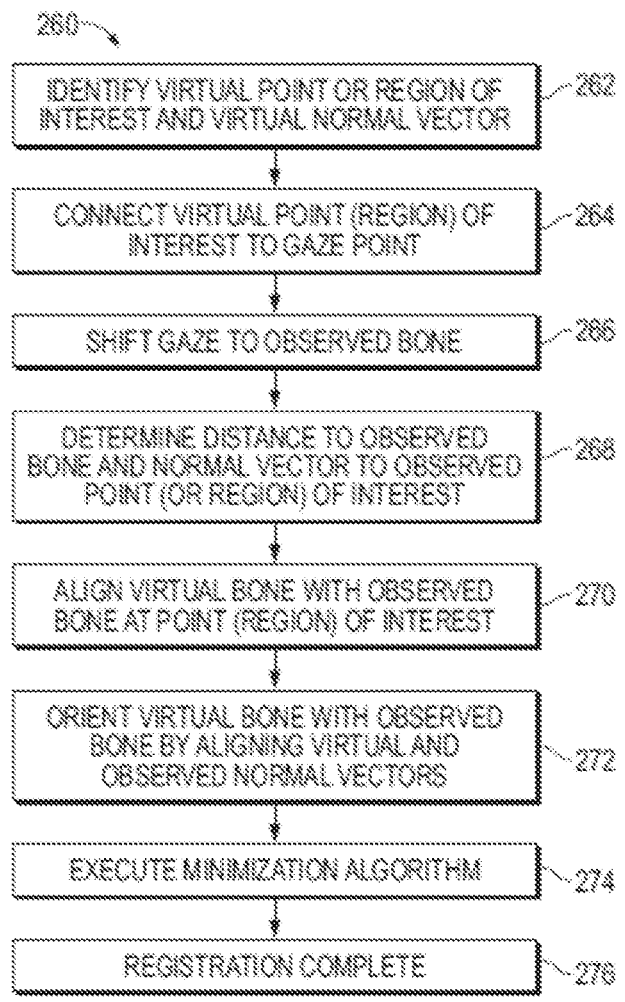
FIG. 10 illustrates an example of a technique for registering a 3-dimensional virtual bone model with an observed real bone structure of a patient during joint repair surgery.

FIG. 10 illustrates an example of a technique 260 for registering a 3D virtual bone model 1008 with a real observed bone structure 252 of a patient. In other words, FIG. 10 is an example of a process flow, e.g., performed by visualization device 213, for registering a virtual bone model with an observed bone that is implemented in a mixed reality system, such as the mixed reality system 212 of FIG. 2. 3D virtual bone model 1008 may be a model of all or part of one or more bones. The process flow of FIG. 10 may be performed as part of the registration process of step 1904 of FIG. 9. The registration process may be carried out in two steps: initialization and optimization (e.g., minimization). During initialization, the user of MR system 212 uses the visualization device 213 in conjunction with information derived from the preoperative virtual planning system 102, the orientation of the user's head (which provides an indication of the direction of the user's eyes (referred to as "gaze" or "gaze line"), rotation of the user's head in multiple directions, sensor data collected by the sensors 530, 532 and/or 533 (or other acquisitions sensors), and/or voice commands and/or hand gestures to visually achieve an approximate alignment of the 3D virtual bone model 1008 with observed bone structure 252. More particularly, at block 262, a point or region of interest on the surface of the virtual bone model 1008 and a virtual normal vector to the point (or region) of interest on the surface of the region are identified during the preoperative planning using the virtual planning system 102.

At block 264, MR system 212 connects the identified point (or region) of interest to the user's gaze point (e.g., a central point in the field of view of visualization device 213). Thus, when the head of the user of visualization device 213 is then moved or rotated, the virtual bone model 1008 also moves and rotates in space.

In the example of a shoulder arthroplasty procedure, the point of interest on the surface of virtual bone model 1008 can be an approximate center of the virtual glenoid that can be determined by using a virtual planning system 102, such as the BLUEPRINT™ planning system. In some examples, the approximate center of the virtual glenoid can be determined using a barycenter find algorithm, with the assistance of machine learning algorithms or artificial intelligence systems or using another type of algorithm. For other types of bone repair/replacement procedures, other points or regions of the bone can be identified and then connected to the user's gaze line or gaze point.

The ability to move and rotate virtual bone model 1008 in space about the user's gaze point alone generally is not sufficient to orient virtual bone model 1008 with the observed bone. Thus, as part of the initialization procedure, MR system 212 also determines the distance between visualization device 213 and a point (or points) on the surface of the observed bone in the field of view of visualization device 213 and the orientation of that surface using sensor data collected from the depth, optical, and motion sensors 530, 532, 533 (block 268). For example, a glenoid is a relatively simple surface because, locally, it can be approximated by a plane. Thus, the orientation of the glenoid surface can be approximated by determining a vector that is normal (i.e., perpendicular) to a point (e.g., a central point) on the surface. This normal vector is referred to herein as the "observed normal vector." It should be understood, however, that other bones may have more complex surfaces, such as the humerus or knee. For these more complex cases, other surface descriptors may be used to determine orientation.

Regardless of the particular bone, distance information can be derived by MR system 212 from depth camera(s) 532. This distance information can be used to derive the geometric shape of the surface of an observed bone. That is, because depth camera(s) 532 provide distance data corresponding to any point in a field of view of depth camera(s) 532, the distance to the user's gaze point on the observed bone can be determined. With this information, the user can then move 3D virtual bone model 1008 in space and approximately align it with the observed bone at a point or region of interest using the gaze point (block 270 in FIG. 10). That is, when the user shifts gaze to observed bone structure 252, virtual bone model 1008 (which is connected to the user's gaze line) moves with the user's gaze. The user can then align 3D virtual bone model 1008 with observed bone structure 252 by moving the user's head (and thus the gaze line), using hand gestures, using voice commands, and/or using a virtual interface to adjust the position of virtual bone model 1008. For instance, once 3D virtual bone model 1008 is approximately aligned with observed bone structure 252, the user may provide a voice command (e.g., "set") that causes MR system 212 to capture the initial alignment. The orientation ("yaw" and "pitch") of the 3D model can be adjusted by rotating the user's head, using hand gestures, using voice commands, and/or using a virtual interface which rotate 3D virtual bone model 1008 about the user's gaze line so that an initial (or approximate) alignment of the virtual and observed objects can be achieved (block 272 in FIG. 10). In this manner, virtual bone model 1008 is oriented with the observed bone by aligning the virtual and observed normal vectors. Additional adjustments of the initial alignment can be performed as needed. For instance, after providing the voice command, the user may provide additional user input to adjust an orientation or a position of virtual bone model 1008 relative to observed bone structure 252. This initial alignment process is performed intraoperatively (or in real time) so that the surgeon can approximately align the virtual and observed bones. In some examples, such as where the surgeon determines that the initial alignment is inadequate, the surgeon may provide user input (e.g., a voice command, such as "reset") that causes MR system 212 to release the initial alignment such that point 280 is again locked to the user's gaze line.

At block 274 of FIG. 10, when the user detects (e.g., sees) that an initial alignment of 3D virtual bone model 1008 with observed bone structure 252 has been achieved (at least approximately), the user can provide an audible or other perceptible indication to inform MR system 212 that a fine registration process (i.e., execution of an optimization (e.g., minimization) algorithm) can be started. For instance, the user may provide a voice command (e.g., "match") that causes MR system 212 to execute a minimization algorithm to perform the fine registration process. The optimization process can employ any suitable optimization algorithm (e.g., a minimization algorithm such as an Iterative Closest Point or genetic algorithm) to perfect alignment of virtual bone model 1008 with observed bone structure 252. At block 276 of FIG. 10, upon completion of execution of the optimization algorithm, the registration procedure is complete.

Figure 11:
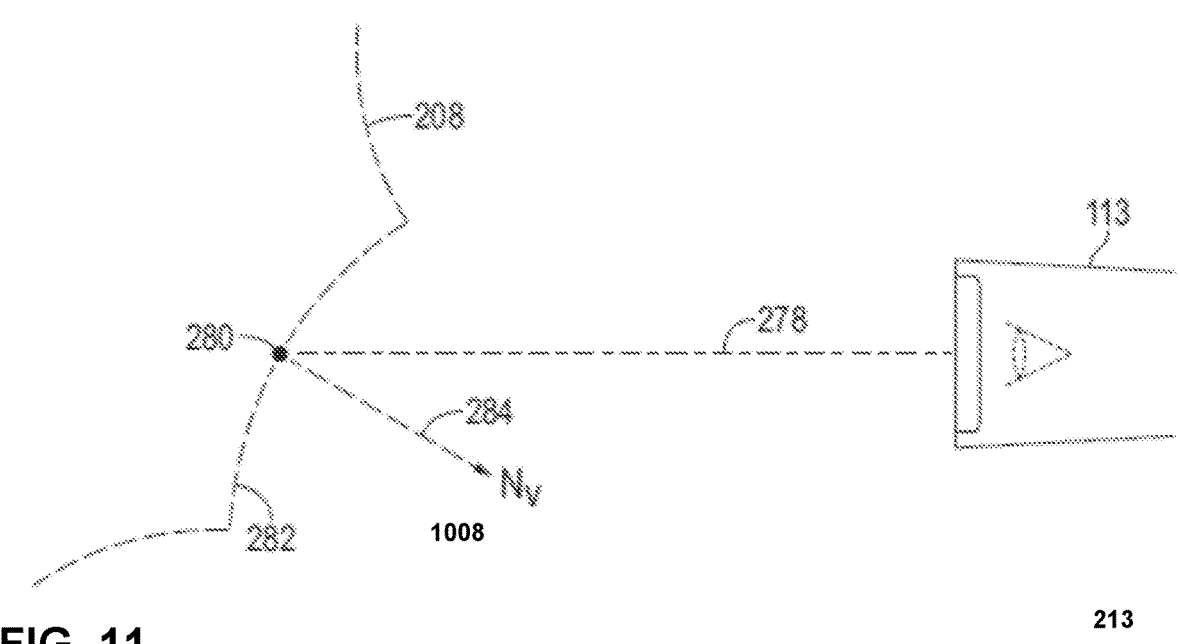
FIG. 11 is a conceptual diagram illustrating steps of an example registration process for a shoulder arthroplasty procedure.
Figure 12:
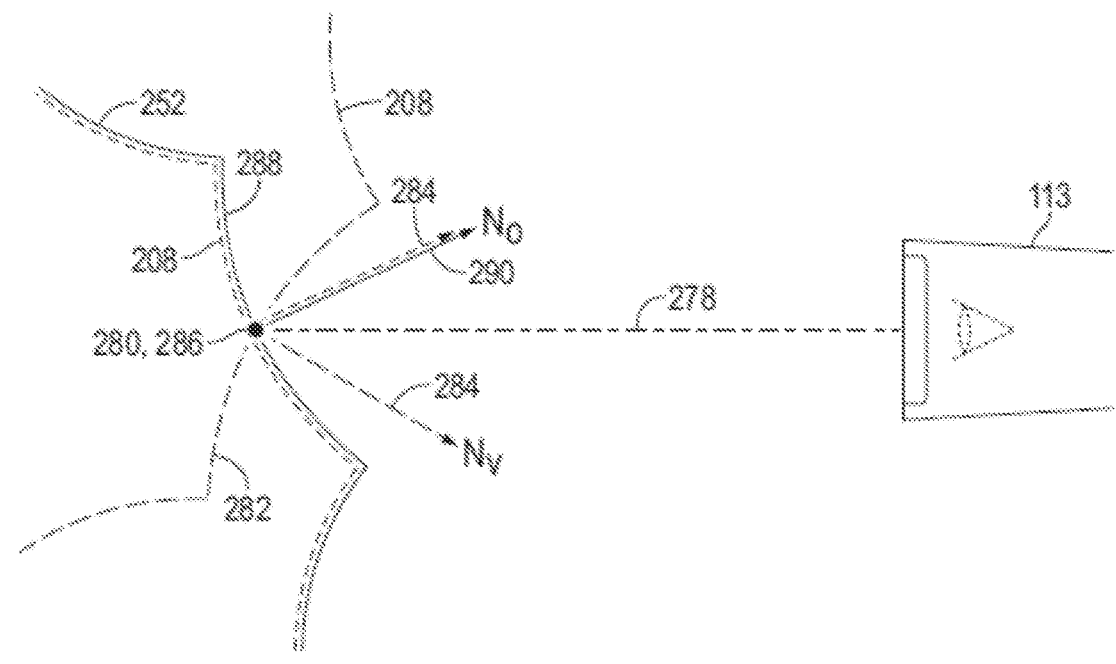
FIG. 12 is a conceptual diagram illustrating additional steps of the example registration process of the shoulder arthroplasty procedure of FIG. 11.

FIG. 11 is a conceptual diagram illustrating steps of an example registration process for a shoulder arthroplasty procedure. FIG. 12 is a conceptual diagram illustrating additional steps of the example registration process of the shoulder arthroplasty procedure of FIG. 11. In FIG. 11, a gaze line 278 of a user of visualization device 213 is connected with the previously identified point of interest (or gaze point) 280 on a surface 282 of 3D virtual bone model 1008 (a glenoid). FIG. 11 also shows a virtual normal vector (Nv) 284 to point 280 on surface 282. In FIG. 12, the user of visualization device 213 shifts gaze line 278 to a region of interest 286 on surface 288 of observed bone structure 252. Because gaze line 278 is connected to the center point 280 of virtual bone model 1008, shifting gaze line 278 aligns virtual center point 280 of virtual bone model 1008 with the observed region of interest 286. However, as shown in FIG. 12, simply shifting the gaze aligns the center points/regions 280, 286, but may not properly orient the virtual bone model 1008 (shown in dashed lines) with observed bone structure 252. Once an observed normal vector (NO) 290 is determined as discussed above, visualization device 213 can adjust the orientation (pitch and yaw) of virtual bone model 1008 until the proper orientation is achieved (shown in dotted lines) and virtual normal vector (VN) 284 is aligned with observed normal vector 290. The user may rotate virtual bone model 1008 around the aligned axes passing through the glenoid for proper alignment of virtual bone model 1008 with the corresponding real bone.

Figure 13:
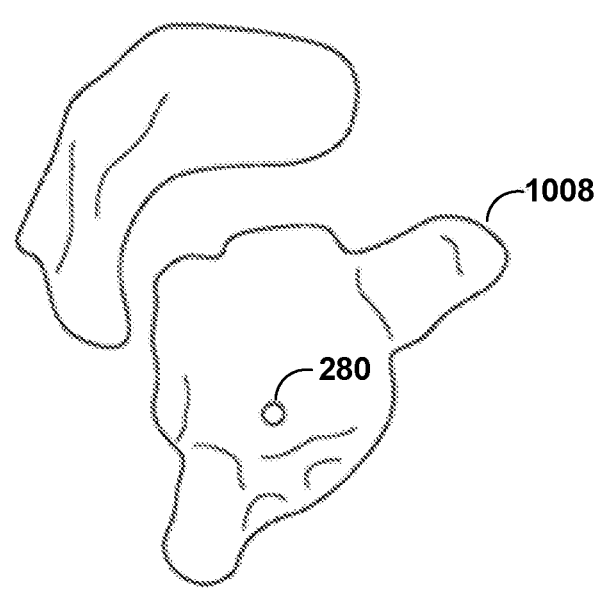
FIG. 13 and FIG. 14 are conceptual diagrams further illustrating an example registration process for a shoulder arthroplasty procedure.
Figure 14:
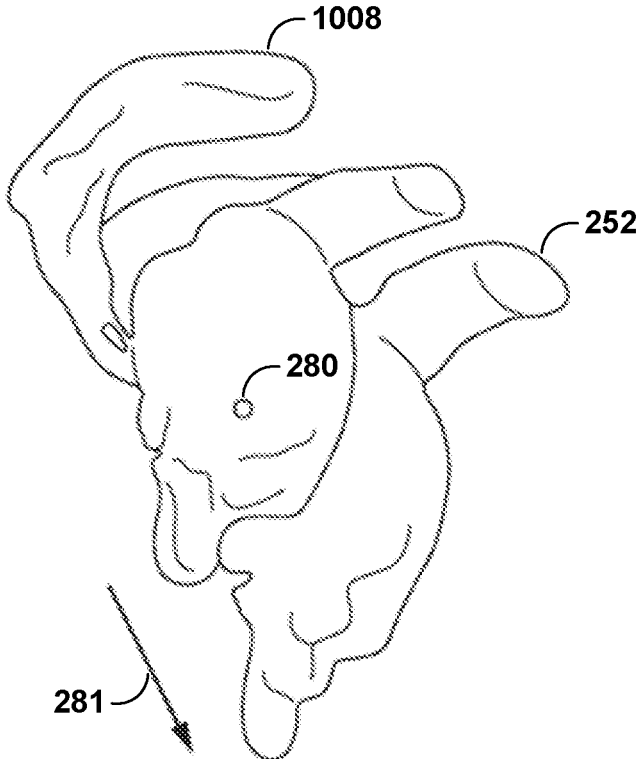

FIG. 13 and FIG. 14 are conceptual diagrams illustrating an example registration process for a shoulder arthroplasty procedure. Similar to the registration process shown in FIG. 11, FIG. 13 illustrates the viewpoint of a user of visualization device 213. As shown in FIG. 13, point of interest 280 is shown on virtual bone model 1008. As discussed above, as the gaze of the user is connected to point 280, the user may move virtual bone model 1008 by shifting their gaze, in which case visualization device 213 detects the gaze shift and moves the virtual bone model in a corresponding manner. As shown in FIG. 14, to align virtual bone model 1008 with observed bone structure 252, the user may shift their gaze in the direction indicated by arrow 281.

For some surgical bone repair procedures, such as shoulder arthroplasties, alignment and orientation of the virtual and observed bone using only the user's gaze can be challenging. These challenges arise due to many factors, including that the bone (e.g., glenoid) is located quite deep under the skin so that even after the surgical incision is made, it can be difficult to position the visualization device 213 close to the bone; shadows may obscure the bone; the entire bone surface of interest may not be visible; and it can be difficult for the user to maintain a steady and stable gaze which can result in instability in the positioning of the virtual bone. In some examples, to address these challenges, the registration procedure can be facilitated through the use of virtual landmark(s) placed at specific location(s) on the bone (e.g., the center of the glenoid for a shoulder arthroplasty procedure). In such examples, the location at which the virtual landmark is placed and the surface normal at that location can be used to automatically determine the initialization transformation (or registration transformation) for the virtual and observed bones. If desired, the alignment achieved between the virtual and observed bone using the virtual landmark can be further adjusted by the user using voice commands, hand gestures, virtual interface buttons, and/or by positioning additional virtual markers at various locations on the bone surface.

Figure 15:
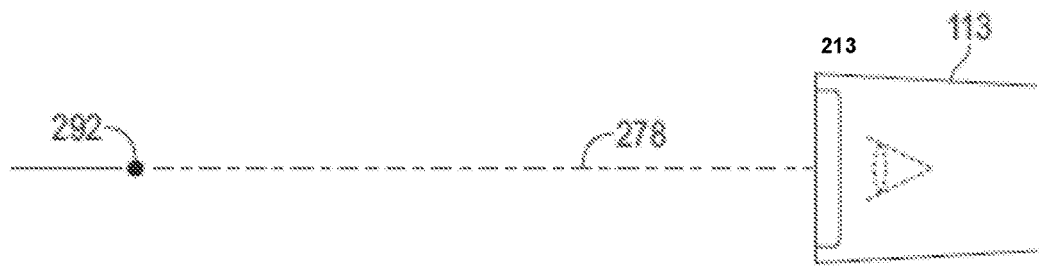
FIG. 15 is a conceptual diagram illustrating an example registration procedure using a virtual marker.
Figure 16:
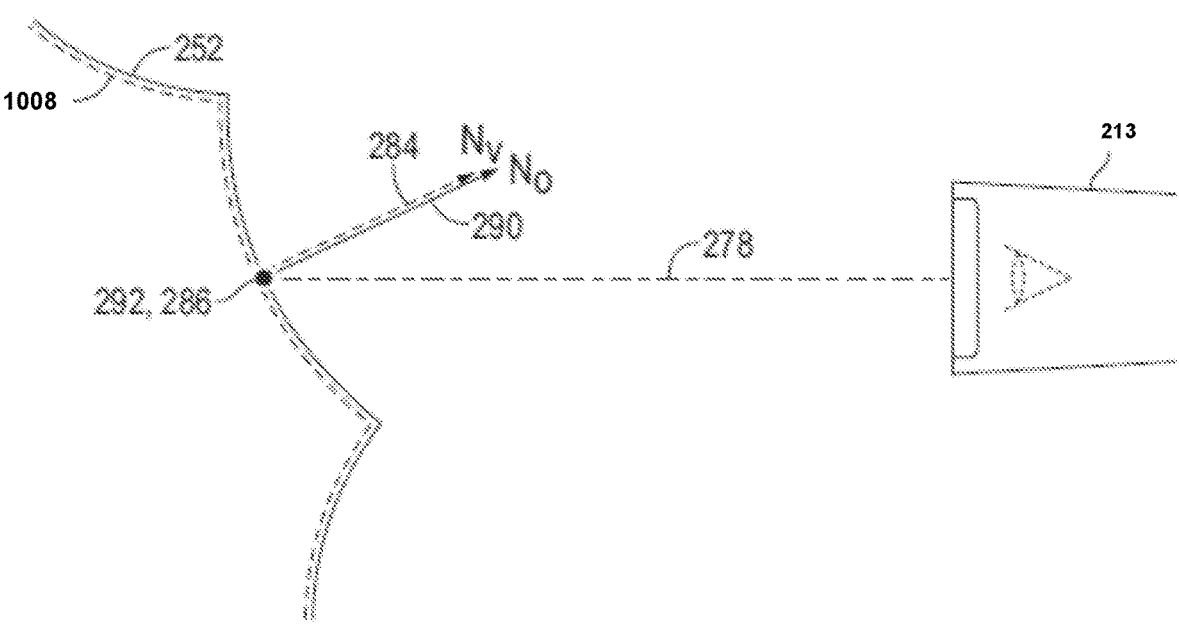
FIG. 16 is a conceptual diagram illustrating additional steps of the example registration procedure of FIG. 15 using a virtual marker.

FIG. 15 illustrates an example registration procedure using a virtual marker 292. FIG. 16 is a conceptual diagram illustrating additional steps of the example registration procedure of FIG. 10 using a virtual marker. In the example of FIG. 15 and FIG. 16, the user of visualization device 213 shifts a gaze line 278 to set virtual marker 292 at a center region 286 (e.g., center point) of observed bone structure 252. With the help of the virtually positioned marker 292, the virtual normal vector 284 and the observed normal vector 290, the initialization transformation between virtual bone model 1008 and observed bone structure 252 can be determined. Then, the optimization algorithm (or registration algorithm) is executed, as described above, in order to obtain an optimal registration between virtual bone model 1008 and observed bone structure 252.

In some examples, the initialization procedure can be implemented based on a region of interest on the bone surface instead of a point of interest. In such examples, the image data collected by the depth and/or optical camera(s) 530, 532 (FIG. 4) of visualization device 213 can be processed to detect surface descriptors that will facilitate identification of the position and orientation of the observed bone and to determine an initialization transformation between the virtual and observed bones.

As discussed above, in some examples, the initialization may be aided by the user (e.g., aided by the user shifting gaze line 278 to set virtual marker 292 at a center region 286 of observed bone structure 252). In some examples, MR system 212 may perform the entire registration process (e.g., including any initialization steps) with minimal or no aid from the user. For instance, MR system 212 may process the image data collected by the depth and/or optical camera(s) 530, 532 (FIG. 4) to automatically identify a location of the anatomy of interest (e.g., observed bone structure 252). As such, MR system 212 may register a virtual model of a portion of anatomy to a corresponding observed portion of anatomy in response to the user looking at the portion of anatomy (e.g., the surgeon, while wearing visualization device 213, may merely look at the portion of anatomy). MR system 212 may automatically identify the location using any suitable technique. For example, MR system 212 may use a machine learned model (i.e., use machine learning, such as a random forest algorithm) to process the image data and identify the location of the anatomy of interest.

In more general terms, the registration method described with reference to FIG. 10 can be viewed as determining a first local reference coordinate system with respect to the 3D virtual model and determining a second local reference coordinate system with respect to the observed real anatomy. In some examples, MR system 212 also can use the optical image data collected from optical cameras 530 and/or depth cameras 532 and/or motion sensors 533 (or any other acquisition sensor) to determine a global reference coordinate system with respect to the environment (e.g., operating room) in which the user is located. In other examples, the global reference coordinate system can be defined in other manners. In some examples, depth cameras 532 are externally coupled to visualization device 213, which may be a mixed reality headset, such as the Microsoft HOLOLENS™ headset or a similar MR visualization device. For instance, depth cameras 532 may be removable from visualization device 213. In some examples, depth cameras 532 are part of visualization device 213, which again may be a mixed reality headset. For instance, depth cameras 532 may be contained within an outer housing of visualization device 213.

The registration process results in generation of a transformation matrix that then allows for translation along the x, y, and z axes of the 3D virtual bone model and rotation about the x, y and z axes in order to achieve and maintain alignment between the virtual and observed bones.

In some examples, to enhance the accuracy and quality of registration, during the initialization stage of the registration process, MR system 212 can compute and display spatial constraints for user head pose and orientation. These constraints can be computed in real time and depend on the position of the user, and/or the orientation, and/or the distance to the observed bone, and/or the depth camera characteristics. For example, MR system 212 may prompt the user to move closer to the observed bone, to adjust the head position so that the user's gaze line is perpendicular to the surface of interest of the observed bone, or to make any other adjustments that can be useful to enhance the registration process and which may depend on the particular surgical application and/or the attributes of the particular anatomy of interest and/or the characteristics of the optical and depth sensors that are employed in MR system 212.

In some examples, depth camera(s) 532 detect distance by using a structured light approach or time of flight of an optical signal having a suitable wavelength. In general, the wavelength of the optical signal is selected so that penetration of the surface of the observed anatomy by the optical signal transmitted by depth camera(s) 532 is minimized. It should be understood, however, that other known or future developed techniques for detecting distance also can be employed.

The registration techniques described herein may be performed for any pair of a virtual model and an observed object. As one example, an MR system may utilize the registration techniques to register a virtual model of a bone to an observed bone. As another example, an MR system may utilize the registration techniques to register a virtual model of an implant to an observed implant. An MR system may utilize the registration techniques to register a virtual model of a tool to an observed tool.

In some examples, an MR system may perform the registration techniques once for a particular pair of a virtual model and an observed object (e.g., within a particular surgical procedure). For instance, an MR system may register a virtual model of a glenoid with an observed glenoid and utilize the registration to provide virtual guidance for multiple steps of a surgical procedure. In some examples, an MR system may perform the registration techniques multiple times for a particular pair of a virtual model and an observed object (e.g., within a particular surgical procedure). For instance, an MR system may first register a virtual model of a glenoid with an observed glenoid and utilize the registration to provide virtual guidance for one or more steps of a surgical procedure. Then, for example, after material has been removed from the glenoid (e.g., via reaming), the MR system may register another virtual model of the glenoid (that accounts for the removed material) with an observed glenoid and use the subsequent registration to provide virtual guidance for one or more other steps of the surgical procedure.

Figure 17:
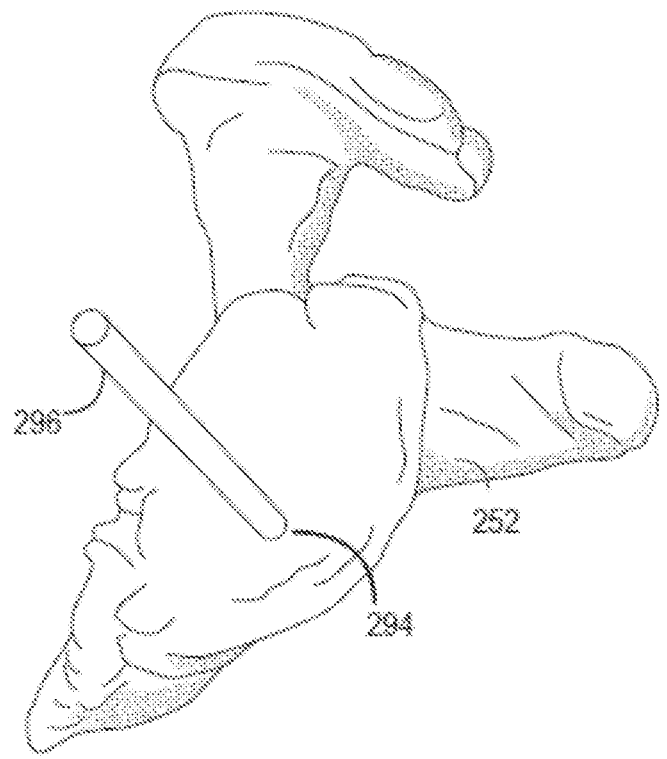
FIG. 17 illustrates an image perceptible to a user when in an augment surgery mode of a mixed reality (MR) system, according to an example of this disclosure.

Once registration is complete the surgical plan can be executed using the Augment Surgery mode of MR system 212. For example, FIG. 17 illustrates an image perceptible to a user when in the augment surgery mode of a mixed reality system, according to an example of this disclosure. As shown in the example of FIG. 17, the surgeon can visualize a virtually planned entry point 294 and drilling axis 296 on observed bone structure 252 and use those virtual images to assist with positions and alignment of surgical tools. Drilling axis 296 may also be referred to as a reaming axis and provides a virtual guide for drilling a hole in the glenoid for placement of a guide pin that will guide a reaming process.

In some circumstances during performance of a surgery, a surgeon may want to view a surgical site from a perspective different from their own. For instance, in an example where the surgeon is drilling a guide hole in a patient's glenoid for a reaming pin, the surgeon may wish to view a drill bit of a drill that the surgeon is using to drill the guide hole from a side perspective relative to the axis of the drill bit. In another example, the surgeon may be using a drill to screw a self-tapping reaming pin into the patient's glenoid. In this example, it may not be necessary for the surgeon to separately drill a guide hole and insert the reaming pin. This may allow the surgeon to better see the angle of entry of a contact component (e.g., the drill bit, reaming pin, etc.) of the drill and how deeply the contact component has penetrated the patient's glenoid and may allow the surgeon to better observe the angle of the contact component. Without the ability to access a side perspective view, the surgeon would have to shift to one side in order to view the contact component from this side perspective while, at the same time, holding the drill steady. However, shifting position while holding the drill steady is difficult to do in practice. Alternatively, mirrors can be placed in the operating room to allow the surgeon to see the surgical site from different perspectives. However, positioning mirrors may be difficult and time consuming for assistants because the assistants cannot easily see what reflections the surgeon is seeing in the mirrors.

This disclosure describes techniques that may address these issues. In one example, intraoperative guidance system 108 (FIG. 1) may determine a location for a first user to stand within an operating room. Additionally, a first MR visualization device (e.g., a MR visualization device of MR system 800B (FIG. 8)) may be configured to be worn by a first user. The first user may be a nurse, assistant, student, surgeon, technician, or other type of person. In this example, the first MR visualization device is further configured to present a first MR visualization, e.g., in the form of virtual positioning guidance, that indicates the location for the first user to stand within the operating room. Additionally, in this example, a second MR visualization device (e.g., a MR visualization device of MR system 800A (FIG. 8)) is configured to be worn by a second user. The second user may be a surgeon, nurse, assistant, student, technician, or other type of person. In this example, the second MR visualization device is further configured to present a second MR visualization that shows images of a surgical site captured by a camera supported by the first user. For instance, the second MR visualization may contain a window the shows the images captured by the camera supported by the first user. The second user may also be able to see the surgical site in addition the images captured by the camera supported by the first user. For instance, the second user may be able to see the surgical site through a holographic waveguide lens that also displays the images captured by the camera supported by the first user.

Figure 18:
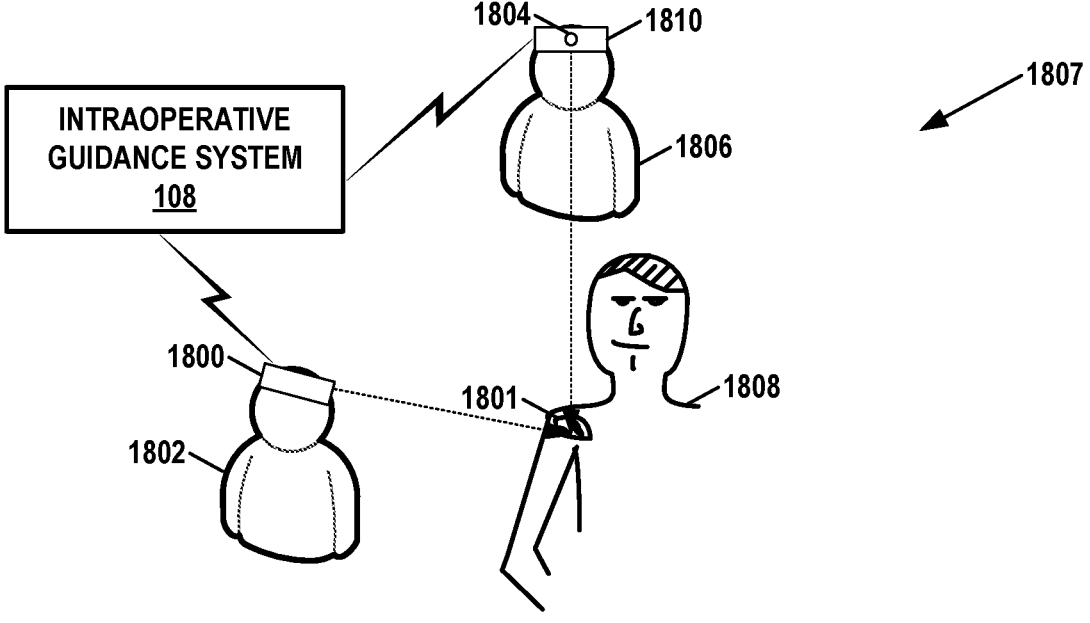
FIG. 18 is a conceptual diagram illustrating an example operating room environment in which an MR visualization device presents an MR visualization that includes images captured by a camera of a different MR visualization device, in accordance with a technique of this disclosure.

FIG. 18 is a conceptual diagram illustrating an example operating room environment in which an MR visualization device 1800 presents an MR visualization that includes images of a surgical site 1801 captured by a camera 1804 of a different MR visualization device, in accordance with a technique of this disclosure. MR visualization device 1800 is worn by a user 1802. In this example, user 1802 may be a surgeon. In the example of FIG. 18, a patient 1808 is undergoing a shoulder surgery. Although this disclosure describes FIG. 18 in the context of a shoulder surgery, the techniques of this disclosure may be applied to other types of surgery on other parts of a patient's body. In FIG. 18, dotted lines correspond to gaze lines of user 1802 and a user 1806.

Furthermore, in the example of FIG. 18, user 1806 is wearing a MR visualization device 1810. In the example of FIG. 18, camera 1804 is coupled to or integrally formed with MR visualization device 1810. For instance, camera 1804 may be integrated into MR visualization device 1810, attached to MR visualization device 1810, or otherwise connected to MR visualization device 1810. In other examples, camera 1804 is not coupled to MR visualization device 1810. For instance, in one example, user 1806 holds camera 1804 in their hands. In another example, camera 1804 may be mounted on a shoulder or chest of user 1806. Thus, camera 108 may be considered to worn or otherwise supported in some way by user 1806. As shown in the example of FIG. 18, the perspective of camera 1804 is different from a perspective of user 1802.

In the example of FIG. 18, intraoperative guidance system 108 is configured to determine a location for user 1806 to stand within an operating room 1807. In some examples, intraoperative guidance system 108 may comprise processing circuitry of one or more computing devices separate from either MR visualization device 1800 and MR visualization device 1810. In such examples, intraoperative guidance system 108 may communicate via wireless communication links with MR visualization device 1800 and MR visualization device 1810. In other examples, the functionality of intraoperative guidance system 108 is implemented in processing circuitry of either or both of MR visualization device 1800 and MR visualization device 1810. In any of these examples, intraoperative guidance system 108 may include one or more processing circuits that perform information processing functions of intraoperative guidance system 108. Such processing circuits may be in one or more of MR visualization device 1800, MR visualization device 1810, or one or more other computing devices.

Intraoperative guidance system 108 may determine a location for user 1806 to stand in one of various ways. For instance, in one example, intraoperative guidance system 108 may obtain a 3D virtual model that includes a 3D virtual model of an anatomical structure (e.g., bone, tissue, etc.) and a 3D virtual line along which a contact component (e.g., drill bit, self-tapping screws, self-tapping pins, anchors, etc.) is planned to be inserted into the anatomical component during a surgery involving the anatomical component. In this example, intraoperative guidance system 108 may generate registration data that describes a mapping between an actual anatomical component of a patient and the 3D virtual model. The registration data may include a transformation matrix that allows for translation along the x, y, and z axes of the 3D virtual model and rotation about the x, y and z axes in order to achieve and maintain alignment between the 3D virtual model and observed objects, such as an observed anatomical component or tool. Example registration processes are described elsewhere in this disclosure. For instance, this disclosure describes example registration processes with respect to FIGS. 10-16. Furthermore, in this example, intraoperative guidance system 108 may determine, based on the registration data, the location for user 1806 to stand within operating room 1807.

Intraoperative guidance system 108 may determine a global reference coordinate system with respect to operating room 1807. For instance, a camera array may be located at an origin point of the global reference coordinate system. The camera array may include one or more depth cameras or stereoscopic optical cameras. The camera array may be integrated into MR visualization device 1800, MR visualization device 1810, or may be separate from either. Furthermore, as part of determining the global reference coordinate system, intraoperative guidance system 108 may determine a distance from MR visualization device 1800 to an initialization point in operating room 1807 that is directly in front of the camera array. The initialization point may be any point in operating room 1807, such as the corner of an operating table, a point on the floor of operating room 1807, a point on a wall of operating room 1807, or otherwise. The direction from MR visualization device 1800 to the initialization point may be the x-axis. The y-axis may be 90-degrees left or right of the x-axis horizontally. The z-axis may be a direction orthogonal to the x-axis and y-axis. The distance from the origin point to the initialization point may be considered a hypotenuse of a triangle defined by: (i) the origin point, (ii) the initialization point, and (iii) a projection of the initialization point onto a x-y reference plane. The x-y reference plane may be defined as a plane horizontally level with the origin point (e.g., parallel to the floor of operating room 1807). Furthermore, intraoperative guidance system 108 may further determine an angle of the hypotenuse of the triangle corresponding to the initialization point relative to a horizontal leg of the triangle. Then, through basic trigonometry, intraoperative guidance system 108 may determine the lengths of the legs of the triangle corresponding to the initialization point. MR visualization device 1800 may then assign a set of 3-dimensional coordinates to the initialization point. For instance, in this example, intraoperative guidance system 108 may assign the x-coordinate for the initialization point and the z-coordinate for the initialization point to be the lengths of the legs of the triangle. Intraoperative guidance system 108 may assign a value of 0 to the y-coordinate of the initialization point.

Additionally, intraoperative guidance system 108 may perform a similar process for a second point in operating room 1807. That is, a first triangle may be defined by (i.a) the origin point, (ii.a), the second point, and (iii.a) a projection of the second point onto an x-y reference plane. The hypotenuse of the first triangle is the line from point (i.a) to point (ii.a). Intraoperative guidance system 108 may determine an angle in the z-dimension between a horizontal leg of the first triangle (i.e., from point (i.a) to point (iii.a)) and the hypotenuse of the triangle. Additionally, a second triangle may be defined by three points: (i.b) the origin point, (ii.b) a projection of the second point onto the x-y reference plane, and (iii.b) a projection of the second point onto an x-z reference plane. The x-z reference plane may be defined as a plane extending in the x-axis and the z-axis. Intraoperative guidance system 108 may also determine an angle in the y-dimension between the point (i.b) and point (iii.b). Intraoperative guidance system 108 may then use this angle in combination with the length of the leg from point (i.b) to point (ii.b) to determine the length of the leg from point (ii.b) to point (iii.b). The distance of the leg from point (ii.b) to point (iii.b) may serve as the y-coordinate of the second point. Intraoperative guidance system 108 may repeat this process for many points in operating room 1807. In this way, intraoperative guidance system 108 may develop a global reference coordinate system for points within operating room 1807.

In examples where MR visualization device 1800 is the portion of intraoperative guidance system 108 that develops the global reference coordinate system, may share this global reference coordinate system with MR visualization device 1810. Alternatively, MR visualization device 1810 may perform the operations to develop the global reference coordinate system and share the global reference coordinate system with MR visualization device 1810. In other examples, both MR visualization device 1800 and MR visualization device 1810 develop global reference coordinate systems independently, share their global reference coordinate systems, and then determine mappings between the global reference coordinate systems. Furthermore, in some examples, intraoperative guidance system 108 may apply one or more transforms to the global reference coordinate system. For instance, intraoperative guidance system 108 may apply a transform to the global reference coordinate system that makes z-coordinates of points on the floor of operating room 1807 have values equal to 0.

FIG. 19 is a conceptual diagram illustrating an example technique for determining a location for user 1806 to stand within operating room 1807, in accordance with a technique of this disclosure. In the example of FIG. 19, to determine the location for user 1806 to stand, intraoperative guidance system 108 may determine a plane 1900 that is orthogonal to a 3D virtual line 1902. In one example, 3D virtual line 1902 may correspond to a planned reaming axis for a glenoid of patient 1808. In another example, a 3D virtual line may correspond to an axis for pin placement for a humeral cutting frame. In other examples, 3D virtual lines may correspond to other planned lines or planes of drilling, hammering, sawing, etc. In the example of FIG. 19, dashed lines indicate that parts of the lines are omitted for scale. Plane 1900 may be established by registering a 3D virtual model of a bone 1906 with bone 1906 (e.g., as described elsewhere in this disclosure).

Plane 1900 intersects a point 1904. Point 1904 is where 3D virtual line 1902 intersects a 3D virtual model of bone 1906. Furthermore, intraoperative guidance system 108 may determine the location for user 1806 to stand within operating room 1807 such that camera 1804 is within plane 1900. Intraoperative guidance system 108 may determine a point 1904 based on the registration data. For instance, intraoperative guidance system 108 may define a virtual coordinate system that indicates the relative positions of virtual elements, such as a 3D virtual model of bone 1906, 3D virtual line 1902, point 1904, and plane 1900. The registration process determines how the virtual coordinate system relates to the global reference coordinate system. Thus, registration data produced by the registration process defines a mapping between the virtual coordinate system and the global reference coordinate system. For instance, the registration data may define a mapping from point 1904 to coordinates in the global reference coordinate system (i.e., a real-world coordinates) of a point on bone 1906 where a contact component is to be inserted into bone 1906. As discussed elsewhere in this disclosure, user 1800 may assist in the registration process by positioning a 3D virtual model of bone 1906 with the actual bone 1906.

In some examples, intraoperative guidance system 108 may obtain information indicating a distance of camera 1804 from the floor of operating room 1807. For instance, intraoperative guidance system 108 may use information from a depth camera of MR visualization device 1810 to determine the distance of camera 1804 from the floor of operating room 1807. In another example, intraoperative guidance system 108 may receive an indication of user input indicating the distance of camera 1804 above the floor of operating room 1807. Intraoperative guidance system 108 may then determine an x-y plane having a real-world z-coordinate corresponding to the distance of camera 1804 above the floor of operating room 1807. Additionally, intraoperative guidance system 108 may use the registration data to determine real-world coordinates of plane 1900. Intraoperative guidance system 108 may then determine where these two planes intersect. Point 1908 is a point on the intersection of these two planes. In an alternative example, intraoperative guidance system 108 may determine the intersection in the virtual coordinate system.

Additionally, in the example of FIG. 19, intraoperative guidance system 108 may determine a point 1910. Point 1910 is a point on the floor of operating room 1807 directly beneath point 1908. In other words, point 1910 is directly lower than point 1908 in the z-axis. That is, in an example where real-world z-axis components are relative to the floor, the x-axis and y-axis components of the real-world coordinates of point 1910 are the same as the x-axis and y-axis components of the real-world coordinates of point 1908, but the z-axis component of the real-world coordinates of point 1910 is equal to 0. Point 1908 is the location for user 1806 to stand within operating room 1807.

In some examples, rather than determine a single point 1910 on the floor of operating room 1807, intraoperative guidance system 108 may generate a map of operating room 1807 that indicates an area on the floor of operating room 1807 that is directly beneath the intersection of the two planes. MR visualization device 1810 may output the map for display to user 1806. In this way, user 1806 may have options on where to stand that still give good views of surgical site 1801.

In another example of how intraoperative guidance system 108 may determine a location for user 1806 to stand, intraoperative guidance system 108 may generate registration data that describes a mapping between a tip of a contact component and operating room 1807. In this example, intraoperative guidance system 108 may then determine, based on the registration data, the location for user 1806 to stand within operating room 1807. This example may be similar to the example described with respect to FIG. 19, except that the tip of the contact component is used in place of point 1904. Thus, intraoperative guidance system 108 may determine a plane that is orthogonal to an axis of the contact component and that intersects a first point, where the first point is at the tip of the contact component. Intraoperative guidance system 108 may then determine the location for user 1806 to stand within operating room 1807 such that the camera is within the plane.

In the example of FIG. 18, MR visualization device 1810 may present a first MR visualization that indicates the location for user 1806 to stand within operating room 1807. In some examples, the first MR visualization comprises a map of operating room 1807 that indicates the location for the first user to stand. The map may be in the form of an overhead map (i.e., a map that shows locations within operating room 1807 from an overhead perspective looking downward). In some examples, the first MR visualization comprises a virtual object fixed to a floor of operating room 1807 at the location for the first user to stand. Thus, from the perspective of user 1806, the location may appear to be marked on the floor of operating room 1807, regardless of where user 1806 looks. In some examples, the first MR visualization may include a virtual object (e.g., an arrow) that appears to user 1806 to float in space above the location where user 1806 is to stand. In some examples, the first MR visualization may include text instructions that direct user 1806 to the location. For instance, in one such example, the text instructions may instruct user 1806 to move 1 meter forward and 100 meters left.

In some examples, MR visualization device 1810 provides feedback to user 1806 regarding a position of user 1806 with respect to the location for user 1806 to stand within operating room 1807. For instance, MR visualization device 1810 may provide a visible message, haptic feedback, audible voice messages, audible sounds, or other types of sensory feedback that provide information to user 1806 to their position relative to the location to stand. The feedback may be positive or negative. For instance, MR visualization device 1810 may provide positive feedback to indicate that user 1806 is correctly standing at the determined location. MR visualization device 1810 may also provide negative feedback to indicate that user 1806 needs to reposition themselves in order to stand at the determined location.

Figure 20:
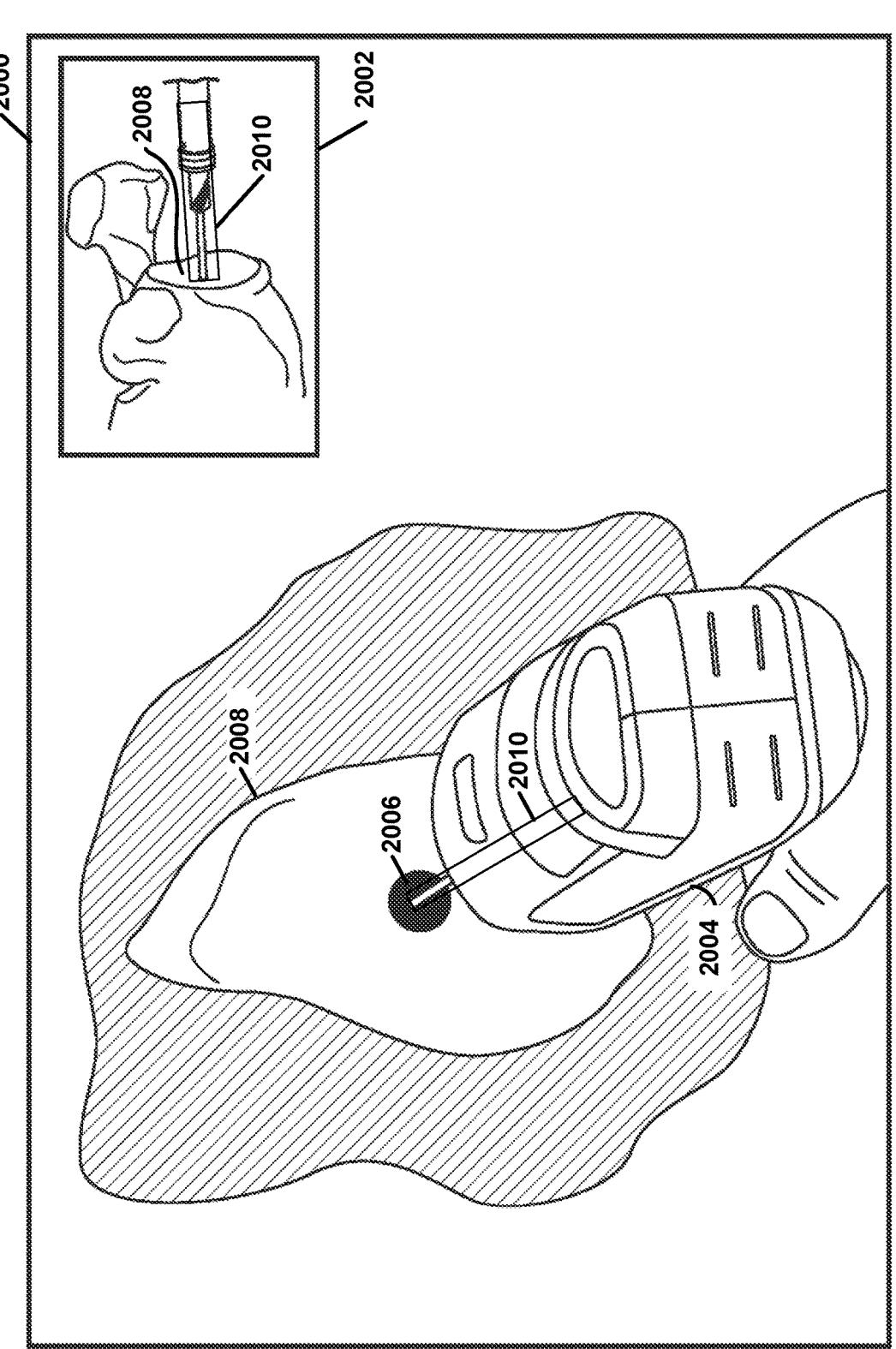
FIG. 20 is a conceptual diagram of an example MR visualization that shows images captured by a camera supported by another user, in accordance with a technique of this disclosure.

MR visualization device 100 may present a second MR visualization that contains a window that shows images of surgical site 1801 captured by camera 1804. FIG. 20 is a conceptual diagram of an example MR visualization 2000 that contains a window 2002 that shows images of surgical site 1801 captured by a camera 1804 (FIG. 18) supported by another user, in accordance with a technique of this disclosure. In some examples, user 1802 may reposition and/or resize window 2002. In the example of FIG. 20, user 1802 (FIG. 18) is performing a surgery on a shoulder of patient 1808. At this stage of the surgery, user 1802 is using a drill 2004 to drill a guide hole 2006 in a glenoid 2008 of patient 1808. In this way, user 1802 may be able to see an angle of insertion of the contact component into glenoid 2008 and may be able to see the depth that the contact component has penetrated glenoid 2008.

As discussed elsewhere in this disclosure, intraoperative guidance system 108 may determine a 3D virtual line, such as 3D virtual line 1902 of FIG. 19) along which a contact component is planned to be inserted into an anatomical component (e.g., bone, muscle, organ, etc.) of the patient during a surgery involving the anatomical component. As shown in the example of FIG. 20, MR visualization 2000 may include a 3D virtual line 2010 along which the contact component of drill 2004 is planned to be inserted into glenoid 2008. In the example of FIG. 20, 3D virtual line 2010 corresponds to a reaming axis for glenoid 2008 of patient 1808. Furthermore, window 2002 may show 3D virtual line 2010 from a perspective of camera 1804. Thus, as shown in the example of FIG. 20, user 1802 may be able to see that the contact component is angled downward slightly too much. Without observing window 2002, user 1802 may have difficultly seeing that the vertical angle is slightly off. In some examples, the MR visualization presented to user 1806 by MR visualization device 1810 may include 3D virtual line 2010.

As noted elsewhere in this disclosure, a computing system (e.g., intraoperative guidance system 108) may generate an information model of a surgery. The information model of the surgery describes a surgical workflow that comprises a series of steps that a surgeon would perform to complete the surgery. During the surgery, the computing system may keep track of which steps of the surgery have been completed. For example, in the example of FIG. 9, the computing system may determine that the incision process (1900), humerus cut process (1902), and registration process (1904) are complete and the remaining steps of the surgery are yet to be completed. In some examples, the computing system may automatically track which steps of the surgery have been completed based on image recognition of the surgical site, determination of which surgical items have been used, and so on. In some examples, the computing system may receive indications of user input, such as hand gestures or voice commands, that indicate the commencement or completion of various steps of the surgery.

In accordance with a technique of this disclosure, intraoperative guidance system 108 may use the surgical plan to determine when to have MR visualization device 1810 indicate that user 1806 should stand at particular locations within operation room 34-107. For example, in response to determining that a step of the surgical plan is complete, intraoperative guidance system 108 may automatically instruct MR visualization device 34-107 to stand at an appropriate position in operating room 1807 for a next step of the surgery. In this way, it may be unnecessary for user 1802 or another person to tell user 1806 to move to the appropriate position for the next step of the surgery.

For instance, in one example, intraoperative guidance system 108 may determine whether a surgical plan specifies that a next step of the surgery is to insert the contact component into the anatomical component. In this example, in response to determining that the surgical plan specifies that the next step of the surgery is to insert the contact component into the anatomical component, intraoperative guidance system 108 may automatically cause MR visualization device 1810 to indicate within the first MR visualization the location for user 1806 to stand within operating room 1807.

FIG. 21 is a flowchart illustrating an example operation for augmenting a view of a user of a MR visualization device, in accordance with one or more techniques of this disclosure. In the example of FIG. 21, a computing system, such as intraoperative guidance system 108, may determine a location for a second user (e.g., user 1806) to stand within an operating room (e.g., operating room 1807) (2100). Furthermore, a second MR visualization device (e.g., visualization device 1810) may be configured to be worn by the second user and may present a MR visualization that indicates the location for the second user to stand within the operating room (2102). A first MR visualization device (e.g., visualization device 1800) may be configured to be worn by a first user (e.g., user 1802) and may present a first MR visualization that contains a window that show images of a surgical site captured by a camera (e.g., camera 1804) supported by the second user (2104).

FIG. 22 is a flowchart illustrating an example operation of MR visualization device 1810 for augmenting a view of a user of another MR visualization device, in accordance with one or more techniques of this disclosure. In the example of FIG. 22, intraoperative guidance system 108, MR visualization device 1810, or another device or system may determine a location for user 1806 to stand within the operating room (2200). For example, MR visualization device 1810 may determine the location for user 1806 to stand in the manner set forth above with respect to FIG. 19.

In some examples, MR visualization device 1810 may determine the location based on information received from a computing device (e.g., a computing device of intraoperative guidance system 108). For instance, MR visualization device 1810 may receive coordinates of the location and MR visualization device 1810 may translate the received coordinates into a coordinate system used by MR visualization device 1810.

Furthermore, in the example FIG. 22, MR visualization device 1810 may present an MR visualization that indicates the location for user 1806 to stand within operating room (2202). For instance, MR visualization device 1810 may present an MR visualization in accordance with any of the examples of this disclosure. The MR visualization may enable user 1806 to also see real objects in operating room 1807. Furthermore, MR visualization device 1810 may include a camera and may send image data representing images of a surgical site captured by the camera of MR visualization device 1810 to MR visualization device 1800, which is configured to be worn by user 1802 (2204). In some examples, MR visualization device 1810 may send the image data directly to MR visualization device 1800 (e.g., via a wireless communication link). In some examples, MR visualization device 1810 may send the image data to MR visualization device 1800 by way of one or more other computing devices, such as a computing device of intraoperative guidance system 108.

Figure 23:
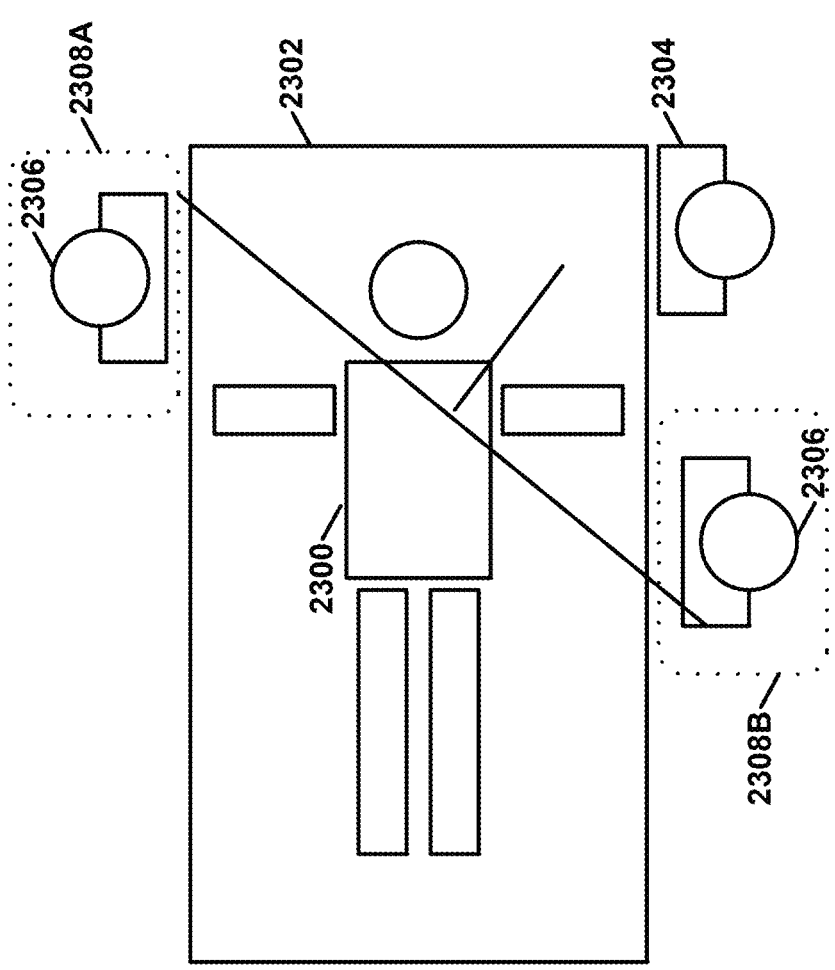
FIG. 23 is a conceptual diagram illustrating an overhead view of an example operating room in accordance with one or more techniques of this disclosure.

FIG. 23 is a conceptual diagram illustrating an overhead view of an example operating room in accordance with one or more techniques of this disclosure. In the example of FIG. 23, a patient 2300 is lying on an operating table 2302. A surgeon 2304 is positioned near the head of patient 2300. In accordance with an aspect of this disclosure, a visualization device may present an MR visualization to a user 2306 instructing user 2306 to stand at a location 2308A or location 2308B. For instance, the visualization device may present an MR visualization to user 2306 that includes a map indicating locations within the operation room where user 2306 is to stand.

Figure 24:
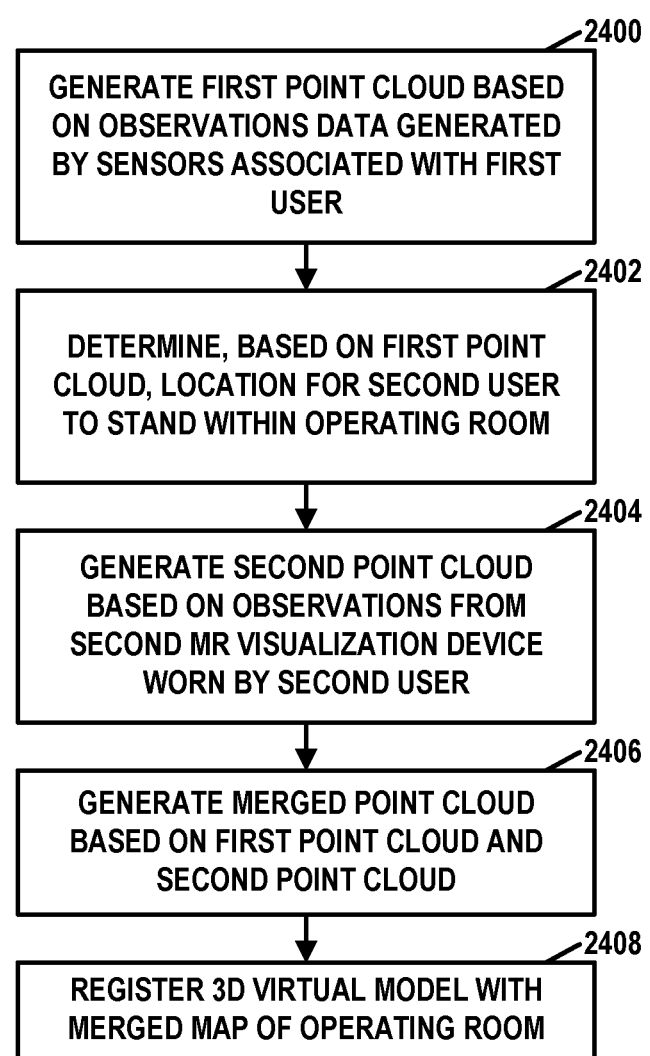
FIG. 24 is a flowchart illustrating an example registration process in accordance with one or more techniques of this disclosure.

FIG. 24 is a flowchart illustrating an example registration process in accordance with one or more techniques of this disclosure. In the example of FIG. 24, intraoperative guidance system 108 is configured to generate a first point cloud based on observation data generated by a set of sensors associated with user 1802 (2400). The first point cloud comprises points having coordinates that indicate locations of a first set of landmarks in operating room 1807. For ease of explanation, this disclosure may refer to the set of sensors associated with user 1802 as the first set of sensors. One or more sensors of the first set of sensors may be integrated into MR visualization device 1800, worn by user 1802, held by user 1802, or otherwise able to generate the observation data from a location of user 1802.

The first set of sensors may include one or more of a variety of different types of sensors. For example, the first set of sensors may include one or more optical cameras, depth sensors, laser range finders, LIDAR sensors, structured light sensors, sonar sensors, or other types of sensors. To generate the first point cloud, intraoperative guidance system 108 may use the observation data to determine, for each time instance of a series of time instances, distances from the first set of sensors to landmarks within operating room 1807 as well as directional information, such as angles between an orientation of the first set of sensors and the landmarks. For instance, intraoperative guidance system 108 may use the observation data to determine a distance to a particular corner of the ceiling of operating room 1807, a distance to a glenoid of patient 1808 in surgical site 1801, a distance to a humeral head of patient 1808 in surgical site 1801, and so on. Intraoperative surgical system 108 may use a Simultaneous Location and Mapping (SLAM) algorithm that constructs the first point cloud based on the observation data generated by the first set of sensors, while also tracking a location of the first set of sensors within operating room 1807.

The first point cloud may express the locations of landmarks within operating room 1807 and the location of the first set of sensors in terms of a set of 3-dimensional coordinates. Intraoperative surgical system 108 may apply one of a variety of SLAM algorithms to determine the first point cloud and a location of the first set of sensors. For example, intraoperative surgical system 108 may apply a SLAM algorithm having a particular filter implementation, an extended Kalman filter implementation, a covariance intersection implementation, a GraphSLAM implementation, an ORB SLAM implementation, or another implementation.

Furthermore, in the example of FIG. 24, intraoperative guidance system 108 may determine, based on the first point cloud, a location for a second user to stand within operating room 1807 (2402). For example, intraoperative guidance system 108 may apply a process that is similar to the technique described above with respect to FIG. 19. That is, intraoperative guidance system 108 may use the first point cloud to determine coordinates of a first plane (e.g., plane 1900) that passes through a point (e.g., point 1904) on an anatomical feature of interest at surgical site 1801. For instance, intraoperative guidance system 108 may register the first point cloud with the anatomical feature of interest at surgical site 1801. Intraoperative guidance system 108 may then determine locations where the first plane intersects a second plane parallel to the floor of operating room 1807 at a height of the user 1806. The second plane may be at a height of camera 1804 above the floor of operating room 1807. In the example of FIG. 19, point 1908 is an example of a point within the intersection between a first plane and a second plane. Intraoperative guidance system 108 may then generate a map (e.g., a heat map) that indicates places for user 1806 to stand within operating room 1807. In this example, the places for user 1806 to stand within operating room 1807 correspond to locations on the floor of operating room 1807 below where the first plane intersects the second plane.

Intraoperative guidance system 108 may be configured to determine the first plane in different ways for different anatomical features of interest. For instance, intraoperative guidance system 108 may determine the first plane in one way when the anatomic feature of interest is the glenoid bone of patient 1808, determine the first plane in a different way when the anatomic feature of interest is the humerus of patient 1808, determine the first plane in yet another different way when the anatomic feature of interest is an ankle of patient 1808. For instance, in the example of FIG. 19, intraoperative guidance system 108 may be configured to determine the first plane as being orthogonal to 3D virtual line 1902, which may correspond to an axis for a planned reaming axis. In an example where the anatomy of interest is a patient's shoulder, the first plane may be orthogonal to a shaft of the patient's humerus.

Additionally, in the example of FIG. 24, intraoperative guidance system 108 is configured to generate a second point cloud based on observation data generated by a set of sensors associated with user 1806 (2404). For ease of explanation, this disclosure may refer to the set of sensors associated with user 1806 as the second set of sensors. One or more sensors of the second set of sensors may be integrated into MR visualization device 1810, worn by user 1806, held by user 1806, or otherwise able to generate the observation data from a location of user 1806. Intraoperative guidance system 108 may generate the second point cloud in the same way that intraoperative guidance system 108 generated the first point cloud.

Next, intraoperative guidance system 108 may generate a merged point cloud of operating room 1807 based on the first point cloud and the second point cloud (2406). For example, intraoperative guidance system 108 may identify a set of landmarks that have determined coordinates in both the first and second point clouds. Example landmarks may include corners of operating room 1807, positions of bones of patient 1808, or other identifiable locations within operating room 1807. In this example, intraoperative guidance system 108 may perform an iterative closest point algorithm based on the identified locations. The iterative closest point algorithm finds a combination of translational and rotational parameters that minimize the sum of distances between corresponding landmarks in the first and second point clouds. For example, consider a basic example where the landmarks in the first point cloud are at coordinates A, B, and C and the same landmarks in the second point cloud are at coordinates A', B', and C'. In this example, the iterative distance minimization algorithm determines a combination of translational and rotational parameters that minimizes $\Delta A + \Delta B + \Delta C$, where $\Delta A$ is the distance between A and A', $\Delta B$ is the distance between B and B', and $\Delta C$ is the distance between C and C'. To minimize the sum of distances between corresponding landmarks in the first and second point clouds, intraoperative guidance system 108 may perform following steps:

1. For each landmark of the first point cloud, determine a corresponding landmark in the second point cloud. The corresponding point may be a closest landmark in the second point cloud.
2. Estimate a combination of rotation and translation parameters using a root mean square point-to-point distance metric minimization technique that best aligns each landmark of the first point cloud to its corresponding landmark in the second point cloud.
3. Transform the landmarks of the first point cloud using the estimated combination of rotation and translation parameters.
4. Iterate steps 1-3 using the transformed landmarks of the first point cloud.

In this example, after performing an appropriate number of iterations, the transformed coordinates of the landmarks of the first point cloud are the coordinates of the merged point cloud. The merged point cloud may also include points of the second point cloud not included in the first point cloud.

The merged point cloud may be more accurate than the first point cloud or the second point cloud because the merged point cloud is based on multiple perspectives of the same scene. For instance, because the humeral head of patient 1801 is oriented away from user 1802, it may be more difficult to determine an accurate position of a point on the humeral head based on the first set of sensors. However, user 1806 may be directed to a position that allows the second set of sensors to have a better perspective on the humeral head. Thus, the second set of sensors may be able to determine the position of the humeral head more accurately.

Furthermore, in the example of FIG. 24, intraoperative guidance system 108 may register a 3D virtual model with the merged point cloud (2408). Intraoperative guidance system 108 may use any of the variety of registration algorithms to register the 3D virtual model with the merged point cloud. In other words, intraoperative guidance system 108 may use a registration algorithm to determine a spatial transformation that aligns points in the 3D virtual model with points in the merged point cloud. For example, intraoperative guidance system 108 may use an iterative closest point algorithm, a robust point matching algorithm, a kernel correlation algorithm, a coherent point drift algorithm, or another type of point set registration algorithm to register the 3D virtual model with the merged point cloud. The 3D virtual model may be a model of bone, such as 3D virtual model 1008 (FIG. 6).

MR visualization device 1800 may output an MR visualization that includes the 3D virtual model registered to a location in operating room 1807. For example, the 3D virtual model may be a virtual model of the glenoid bone of patient 1808 and the MR visualization may show the 3D virtual model at the actual glenoid bone of patient 1808. In another example, the 3D virtual model may be a 3D object representing a reaming axis for reaming a glenoid bone of patient 1808 and the MR visualization may show the reaming axis such that one end of the reaming axis is at an appropriate location on the glenoid bone of patient 1808. In some examples, the MR visualization concurrently includes one or more images of surgical site 1801 captured by camera 1804 supported by user 1806. In other examples, or at particular times, the MR visualization does not concurrently include the 3D virtual model and the one or more images of surgical site 1801 captured by camera 1804.

In some examples, the one or more images of surgical site 1801 that are captured by camera 1804 and displayed in the MR visualization displayed by MR visualization device 1800 include the 3D virtual model, which has been registered to the merged point cloud. In other words, the images may show the 3D virtual model, along with the real anatomy of patient 1808 as user 1806 may see the 3D virtual model and real anatomy of patient 1808. This may be especially helpful to user 1802 when the 3D virtual model represents a reaming axis and user 1802 is attempting to properly align a drill bit with the reaming axis. That is because user 1802 may better able to check whether the angle of the drill bit relative to the reaming axis when user 1802 is able to see the angle of the drill bit relative to the reaming axis from multiple positions.

The following is a non-limiting list of examples that are in accordance with one or more techniques of this disclosure.

Example 1. A mixed reality (MR) surgical system, comprising: a first MR visualization device configured to be worn by the first user; a second MR visualization device configured to be worn by a second user; an intraoperative guidance system comprising one or more processing circuits configured to determine a location for the second user to stand within an operating room, wherein: the second MR visualization device is further configured to present a first MR visualization that indicates the location for the second user to stand within the operating room; and the first MR visualization device is further configured to present a second MR visualization that shows one or more images of a surgical site captured by a camera supported by the second user.

Example 2. The MR surgical system of example 1, wherein the one or more processing circuits of the intraoperative guidance system are configured to: obtain a 3-dimensional (3D) virtual model that includes a 3D virtual model of an anatomical component and a 3D virtual line along which a contact component is planned to be inserted into the anatomical component during a surgery involving the anatomical component; generate registration data that describes a mapping between an actual anatomical component of a patient and the 3D virtual model; and determine, based on the registration data, the location for the second user to stand within the operating room.

Example 3. The MR surgical system of example 2, wherein the one or more processing circuits of the intraoperative guidance system are configured such that, as part of determining the location for the second user to stand within the operating room, the one or more processing circuits: determine a plane that is orthogonal to the 3D virtual line and that intersects a first point, the first point being where the 3D virtual line intersects the 3D virtual model of the anatomical component; and determine the location for the second user to stand within the operating room such that the camera is within the plane.

Example 4. The MR surgical system of example 3, wherein the one or more processing circuits of the intraoperative guidance system are configured such that, as part of determining the location for the second user to stand within the operating room, the one or more processing circuits: determine a second point based on the registration data, the second point being within the plane and being at a distance of the camera above a floor of the operating room; and determine a third point, the third point being on the floor of the operating room directly beneath the second point, wherein the third point is the location for the second user to stand within the operating room.

Example 5. The MR surgical system of any of examples 1-4, wherein the one or more processing circuits of the intraoperative guidance system are configured to determine a 3D virtual line along which a contact component is planned to be inserted into an anatomical component of the patient during a surgery involving the anatomical component, and wherein the first MR visualization includes the 3D virtual line.

Example 6. The MR surgical system of any of examples 1-5, wherein the one or more processing circuits of the intraoperative guidance system are configured to determine a 3D virtual line along which a contact component is planned to be inserted into an anatomical component of the patient during a surgery involving the anatomical component, and wherein the second MR visualization includes the 3D virtual line.

Example 7. The MR surgical system of any of examples 1-6, wherein the one or more processing circuits of the intraoperative guidance system are configured to determine a 3D virtual line along which a contact component is planned to be inserted into an anatomical component of the patient during a surgery involving the anatomical component, and wherein the window in the second MR visualization shows the 3D virtual line from a perspective of the camera.

Example 8. The MR surgical system of any of examples 2-7, wherein the 3D virtual line corresponds to a reaming axis for a glenoid of the patient.

Example 9. The MR surgical system of any of examples 2-7, wherein the 3D virtual line corresponds to an axis for pin placement for a humeral cutting frame.

Example 10. The MR surgical system of any of examples 1-9, wherein the perspective of the camera is different from a perspective of the first user.

Example 11. The MR surgical system of any of examples 1-10, wherein the one or more processing circuits of the intraoperative guidance system are configured to: generate registration data that describes a mapping between a tip of a contact component and the operating room; and determine, based on the registration data, the location for the second user to stand within the operating room.

Example 12. The MR surgical system of example 11, wherein the one or more processing circuits of the intraoperative guidance system are configured such that, as part of determining the location for the second user to stand within the operating room, the one or more processing circuits: determine a plane that is orthogonal to an axis of the contact component and that intersects a first point, the first point being at the tip of the contact component; and determine the location for the second user to stand within the operating room such that the camera is within the plane.

Example 13. The MR surgical system of any of examples 1-12, wherein the first MR visualization comprises a map of the operating room that indicates the location for the second user to stand.

Example 14. The MR surgical system of any of examples 1-13, wherein the first MR visualization comprises a virtual object fixed to a floor of the operating room at the location for the second user to stand.

Example 15. The MR surgical system of any of examples 1-14, wherein the first MR visualization device is configured to provide feedback to the second user regarding a position of the second user with respect to the location for the second user to stand within the operating room.

Example 16. The MR surgical system of any of examples 1-15, wherein the one or more processing circuits of the intraoperative guidance system are configured to: determine whether a surgical plan specifies that a next step of the surgery is to insert the contact component into the anatomical component; and in response to determining that the surgical plan specifies that the next step of the surgery is to insert the contact component into the anatomical component, automatically cause the first MR visualization device to indicate within the first MR visualization the location for the second user to stand within the operating room.

Example 17. The MR surgical system of any of examples 1-16, wherein the camera is coupled to the first MR visualization device.

Example 18. The MR surgical system of any of examples 1-17, wherein the one or more processing circuits of the intraoperative guidance system are configured to: determine a first plane that passes through a point on an anatomical feature of interest at the surgical site; determine locations where the first plane interests a second plane, the second plane being a plane parallel to a floor of the operating room at a height of the camera supported by the second user; and generate a map that indicates places for the second user to stand within the operating room that correspond to locations on the floor of the operating room below the locations where the first plane intersects the second plane.

Example 19. The MR surgical system of any of examples 1-18, wherein: the first MR visualization device is configured to generate a first point cloud based on observation data generated by a set of sensors associated with the first user, the first point cloud comprising points having coordinates indicating locations of a first set of landmarks in the operating room; the one or more processing circuits are configured to determine, based on the first point cloud, the location for the second user to stand within the operating room; the second MR visualization device is configured to generate a second point cloud based on observations data generated by a set of sensors associated with the second user, the second point cloud comprising points having coordinates indicating locations of a second set of landmarks in the operating room; the one or more processing circuits of the intraoperative guidance system are further configured to: generate a merged point cloud based on the first point cloud and the second point cloud; and register a 3D virtual model with the merged point cloud, and at least one of: the second MR visualization includes the 3D virtual model registered to a location in the operating room, or the one or more images of the surgical site captured by the camera supported by the second user include the 3D virtual model.

Example 20. A method for augmenting a view of a first user of a first mixed reality (MR) visualization device, the method comprising: determining a location for a second user to stand within an operating room; presenting, by a second MR visualization device configured to be worn by the second user, a MR visualization that indicates the location for the second user to stand within the operating room; and presenting, by the first MR visualization device, a MR visualization that contains a window that shows images of a surgical site captured by a camera supported by the second user while the second user is at the determined location.

Example 21. The method of example 20, further comprising: obtaining a 3-dimensional (3D) virtual model that includes a 3D virtual model of an anatomical component and a 3D virtual line along which a contact component is planned to be inserted into the anatomical component during a surgery involving the anatomical component; generating registration data that describes a mapping between an actual anatomical component of a patient and the 3D virtual model; and determining, based on the registration data, the location for the second user to stand within the operating room.

Example 22. The method of any of examples 20-21, wherein determining the location for the second user to stand within the operating room comprises: determining a plane that is orthogonal to the 3D virtual line and that intersects a first point, the first point being where the 3D virtual line intersects the 3D virtual model of the anatomical component; and determining the location for the second user to stand within the operating room such that the camera is within the plane.

Example 23. The method of example 22, wherein determining the location for the second user to stand within the operating room comprises: determining a second point based on the registration data, the second point being within the plane and being at a distance of the camera above a floor of the operating room; and determining a third point, the third point being on the floor of the operating room directly beneath the second point, wherein the third point is the location for the second user to stand within the operating room.

Example 24. The method of any of examples 20-23, further comprising determining a 3D virtual line along which a contact component is planned to be inserted into an anatomical component of the patient during a surgery involving the anatomical component, wherein the first MR visualization includes the 3D virtual line.

Example 25. The method of any of examples 20-24, wherein the method further comprises determining a 3D virtual line along which a contact component is planned to be inserted into an anatomical component of the patient during a surgery involving the anatomical component, and wherein the second MR visualization includes the 3D virtual line.

Example 26. The method of any of examples 20-25, wherein the method further comprises determining a 3D virtual line along which a contact component is planned to be inserted into an anatomical component of the patient during a surgery involving the anatomical component, and wherein the window in the second MR visualization shows the 3D virtual line from a perspective of the camera.

Example 27. The method of any of examples 20-26, wherein the 3D virtual line corresponds to a reaming axis for a glenoid of the patient.

Example 28. The method of any of examples 21-26, wherein the 3D virtual line corresponds to an axis for pin placement for a humeral cutting frame.

Example 29. The method of any of examples 20-28, wherein the perspective of the camera is different from a perspective of the first user.

Example 30. The method of any of examples 20-29, further comprising: generating registration data that describes a mapping between a tip of a contact component and the operating room; and determining, based on the registration data, the location for the second user to stand within the operating room.

Example 31. The method of example 30, wherein determining the location for the second user to stand within the operating room comprises: determining a plane that is orthogonal to an axis of the contact component and that intersects a first point, the first point being at the tip of the contact component; and determining the location for the second user to stand within the operating room such that the camera is within the plane.

Example 32. The method of any of examples 20-31, wherein the MR visualization presented by the second MR visualization device comprises a map of the operating room that indicates the location for the second user to stand.

Example 33. The method of any of examples 20-32, wherein the MR visualization presented by the second MR visualization device comprises a virtual object fixed to a floor of the operating room at the location for the second user to stand.

Example 34. The method of any of examples 20-33, further comprising providing, by the second MR visualization device, feedback to the second user regarding a position of the second user with respect to the location for the second user to stand within the operating room.

Example 35. The method of any of examples 20-34, further comprising: determining whether a surgical plan specifies that a next step of the surgery is to insert the contact component into the anatomical component; and in response to determining that the surgical plan specifies that the next step of the surgery is to insert the contact component into the anatomical component, automatically causing the second MR visualization device to indicate within the MR visualization presented by the second MR visualization device the location for the second user to stand within the operating room.

Example 36. The method of any of examples 20-35, wherein the camera is coupled to the second MR visualization device.

Example 37. The method of any of examples 20-36, further comprising: determining a first plane that passes through a point on an anatomical feature of interest at the surgical site; determining locations where the first plane interests a second plane, the second plane being a plane parallel to a floor of the operating room at a height of the camera supported by the second user; and generating a map that indicates places for the second user to stand within the operating room that correspond to locations on the floor of the operating room below the locations where the first plane intersects the second plane.

Example 38. The method of any of examples 20-37, wherein the method further comprises: generating, by the first MR visualization device, a first point cloud, the first point cloud comprising points having coordinates indicating locations of a first set of landmarks in the operating room; generating, by the second MR visualization device, a second point cloud, the first point cloud comprising points having coordinates indicating locations of a first set of landmarks in the operating room; generating a merged point cloud based on the first point cloud and the second point cloud; and registering a 3D virtual model with the merged point cloud, and wherein at least one of: the MR visualization presented by the first MR visualization device includes the 3D virtual model registered to a location in the operating room, or the one or more images of the surgical site captured by the camera supported by the second user include the 3D virtual model.

Example 39. A method for augmenting a view of a first user of a first Mixed Reality (MR) visualization device, the method comprising: determining a location for a second user to stand within an operating room; presenting, by a second MR visualization device, a first MR visualization that indicates a location for the second user to stand within the operating room; and sending, by the second MR visualization device, image data representing images of a surgical site captured by a camera of the second MR visualization device to the first MR visualization device.

Example 40. The method of example 39, further comprising the methods of any of examples 20-38.

Example 41. A mixed reality visualization device configured to perform the methods of any of examples 39-40.

Example 42. A computer-readable data storage medium having instructions stored thereon that, when executed, cause an intraoperative guidance system, a first Mixed Reality (MR) visualization device, and a second MR visualization device to perform the methods of any of examples 20-40.

Example 43. A mixed reality (MR) surgical system for augmenting a view of a first user of a first mixed reality (MR) visualization device, comprising: means for determining a location for a second user to stand within an operating room; means for presenting a MR visualization to the second user that indicates the location for the second user to stand within the operating room; and means for presenting a MR visualization to the first user, the MR visualization presented to the first user containing a window that show images of a surgical site captured by a camera supported by the second user.

Example 44. The MR surgical system of example 32, further comprising means for performing the methods of any of examples 20-40.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. A mixed reality (MR) surgical system, comprising:
a first MR visualization device configured to be worn by a first user;
a second MR visualization device configured to be worn by a second user;
an intraoperative guidance system comprising one or more processing circuits configured to determine a location for the second user to stand within an operating room, wherein:
the first MR visualization device is further configured to present a first MR visualization that shows one or more images of a surgical site captured by a camera supported by the second user; and
the second MR visualization device is further configured to present a second MR visualization that indicates the location for the second user to stand within the operating room, wherein one or more of: the second MR visualization comprises a first virtual object fixed to a floor of the operating room at the location, the second MR visualization comprises a map of the operating room indicating the location, the second MR visualization comprises a second virtual object that appears to the second user to float in a space above the location, or the second MR visualization includes text instructions that direct the second user to the location.

2. The MR surgical system of claim 1, wherein the one or more processing circuits of the intraoperative guidance system are configured to:
obtain a 3-dimensional (3D) virtual model that includes a 3D virtual model of an anatomical component and a 3D virtual line along which a contact component is planned to be inserted into the anatomical component during a surgery involving the anatomical component;
generate registration data that describes a mapping between an actual anatomical component of a patient and the 3D virtual model; and
determine, based on the registration data, the location for the second user to stand within the operating room.

3. The MR surgical system of claim 2, wherein the one or more processing circuits of the intraoperative guidance system are configured such that, as part of determining the location for the second user to stand within the operating room, the one or more processing circuits:
determine a plane that is orthogonal to the 3D virtual line and that intersects a first point, the first point being where the 3D virtual line intersects the 3D virtual model of the anatomical component; and
determine the location for the second user to stand within the operating room such that the camera is within the plane.

4. The MR surgical system of claim 3, wherein the one or more processing circuits of the intraoperative guidance system are configured such that, as part of determining the location for the second user to stand within the operating room, the one or more processing circuits:
determine a second point based on the registration data, the second point being within the plane and being at a distance of the camera above the floor of the operating room; and determine a third point, the third point being on the floor of the operating room directly beneath the second point, wherein the third point is the location for the second user to stand within the operating room.

5. The MR surgical system of claim 2, wherein the 3D virtual line corresponds to a reaming axis for a glenoid of the patient.

6. The MR surgical system of claim 2, wherein the 3D virtual line corresponds to an axis for pin placement for a humeral cutting frame.

7. The MR surgical system of claim 2, wherein the one or more processing circuits of the intraoperative guidance system are configured to:

determine whether a surgical plan specifies that a next step of the surgery is to insert the contact component into the anatomical component; and in response to determining that the surgical plan specifies that the next step of the surgery is to insert the contact component into the anatomical component, automatically cause the second MR visualization device to indicate within the second MR visualization the location for the second user to stand within the operating room.

8. The MR surgical system of claim 1, wherein the one or more processing circuits of the intraoperative guidance system are configured to determine a 3D virtual line along which a contact component is planned to be inserted into an anatomical component of a patient during a surgery involving the anatomical component, and wherein the second MR visualization includes the 3D virtual line.

9. The MR surgical system of claim 1, wherein the one or more processing circuits of the intraoperative guidance system are configured to determine a 3D virtual line along which a contact component is planned to be inserted into an anatomical component of a patient during a surgery involving the anatomical component, and wherein the first MR visualization includes the 3D virtual line.

10. The MR surgical system of claim 1, wherein the one or more processing circuits of the intraoperative guidance system are configured to determine a 3D virtual line along which a contact component is planned to be inserted into an anatomical component of a patient during a surgery involving the anatomical component, and wherein the one or more images in the first MR visualization show the 3D virtual line from a perspective of the camera.

11. The MR surgical system of claim 1, wherein a perspective of the camera is different from a perspective of the first user.

12. The MR surgical system of claim 1, wherein the one or more processing circuits of the intraoperative guidance system are configured to:

generate registration data that describes a mapping between a tip of a contact component and the operating room; and determine, based on the registration data, the location for the second user to stand within the operating room.

13. The MR surgical system of claim 12, wherein the one or more processing circuits of the intraoperative guidance system are configured such that, as part of determining the location for the second user to stand within the operating room, the one or more processing circuits:

determine a plane that is orthogonal to an axis of the contact component and that intersects a first point, the first point being at the tip of the contact component; and determine the location for the second user to stand within the operating room such that the camera is within the plane.

14. The MR surgical system of claim 1, wherein the second MR visualization device is configured to provide feedback to the second user regarding a position of the second user with respect to the location for the second user to stand within the operating room.

15. The MR surgical system of claim 1, wherein the one or more processing circuits of the intraoperative guidance system are configured to:

determine a first plane that passes through a point on an anatomical feature of interest at the surgical site;

determine locations where the first plane intersects a second plane, the second plane being a plane parallel to the floor of the operating room at a height of the camera supported by the second user; and generate the map such that the map indicates places for the second user to stand within the operating room that correspond to locations on the floor of the operating room below the locations where the first plane intersects the second plane.

16. The MR surgical system of claim 1, wherein:

the location is a first location;

the first MR visualization device is configured to generate a first point cloud based on first observation data generated by a set of sensors associated with the first user, the first point cloud comprising points having coordinates indicating locations of a first set of landmarks in the operating room;

the one or more processing circuits are configured to determine the first location based on the first point cloud;

the second MR visualization device is configured to generate a second point cloud based on second observation data generated by a set of sensors associated with the second user, the second point cloud comprising points having coordinates indicating locations of a second set of landmarks in the operating room;

the one or more processing circuits of the intraoperative guidance system are further configured to:

generate a merged point cloud based on the first point cloud and the second point cloud; and register a 3D virtual model with the merged point cloud, and at least one of:

the first MR visualization includes the 3D virtual model registered to a second location in the operating room, or the one or more images of the surgical site captured by the camera supported by the second user include the 3D virtual model.

17. A method for augmenting a view of a first user of a first mixed reality (MR) visualization device, the method comprising:

presenting, by a second MR visualization device configured to be worn by a second user, a second MR visualization that indicates a location for the second user to stand within an operating room, wherein one or more of: the second MR visualization comprises a first virtual object fixed to a floor of the operating room at the location, the second MR visualization comprises a map of the operating room indicating the location, the second MR visualization comprises a second virtual object that appears to the second user to float in a space above the location, or the second MR visualization includes text instructions that direct the second user to the location; and presenting, by the first MR visualization device, a first MR visualization that shows one or more images of a surgical site captured by a camera supported by the second user while the second user is at the location.

18. The method of claim 17, further comprising:

obtaining a 3-dimensional (3D) virtual model that includes a 3D virtual model of an anatomical component and a 3D virtual line along which a contact component is planned to be inserted into the anatomical component during a surgery involving the anatomical component;

generating registration data that describes a mapping between an actual anatomical component of a patient and the 3D virtual model; and determining, based on the registration data, the location for the second user to stand within the operating room.

19. The method of claim 18, further comprising:

determining a plane that is orthogonal to the 3D virtual line and that intersects a first point, the first point being where the 3D virtual line intersects the 3D virtual model of the anatomical component; and determining the location for the second user to stand within the operating room such that the camera is within the plane.

20. The method of claim 19, further comprising:

determining a second point based on the registration data, the second point being within the plane and being at a distance of the camera above the floor of the operating room; and determining a third point, the third point being on the floor of the operating room directly beneath the second point, wherein the third point is the location for the second user to stand within the operating room.

21. The method of claim 17, further comprising determining a 3D virtual line along which a contact component is planned to be inserted into an anatomical component of a patient during a surgery involving the anatomical component, wherein the first MR visualization includes the 3D virtual line.

22. The method of claim 17, wherein the method further comprises determining a 3D virtual line along which a contact component is planned to be inserted into an anatomical component of a patient during a surgery involving the anatomical component, and wherein the second MR visualization includes the 3D virtual line.

23. The method of claim 17, wherein the method further comprises determining a 3D virtual line along which a contact component is planned to be inserted into an anatomical component of a patient during a surgery involving the anatomical component, and wherein the one or more images in the first MR visualization show the 3D virtual line from a perspective of the camera.

24. The method of claim 17, wherein the location is a first location and the method further comprises:

generating, by the first MR visualization device, a first point cloud, the first point cloud comprising points having coordinates indicating locations of a first set of landmarks in the operating room;

generating, by the second MR visualization device, a second point cloud, the second point cloud comprising points having coordinates indicating locations of a second set of landmarks in the operating room;

generating a merged point cloud based on the first point cloud and the second point cloud; and registering a 3D virtual model with the merged point cloud, and wherein at least one of:

the first MR visualization includes the 3D virtual model registered to a second location in the operating room, or the one or more images of the surgical site captured by the camera supported by the second user include the 3D virtual model.

25. One or more non-transitory computer-readable data storage media having instructions stored thereon that, when executed, cause:

an interoperative guidance system to determine a location for a second user to stand within an operating room;

a second MR visualization device configured to be worn by the second user to present a second MR visualization that indicates the location for the second user to stand within the operating room, wherein one or more of: the second MR visualization comprises a first virtual object fixed to a floor of the operating room at the location, the second MR visualization comprises a map of the operating room indicating the location, the second MR visualization comprises a second virtual object that appears to the second user to float in a space above the location, or the second MR visualization includes text instructions that direct the second user to the location; and a first MR visualization device to present a first MR visualization that shows one or more images of a surgical site captured by a camera supported by the second user while the second user is at the location.

* * * * *